United States Patent [19]

Nick et al.

[11] Patent Number: 5,985,633
[45] Date of Patent: Nov. 16, 1999

[54] HUMAN MANGANESE SUPEROXIDE DISMUTASE PROTEINS

[75] Inventors: Harry S. Nick; David N. Silverman, both of Gainesville, Fla.

[73] Assignee: University of Florida, Gainesville, Fla.

[21] Appl. No.: 08/927,230

[22] Filed: Sep. 10, 1997

[51] Int. Cl.[6] .............................. C12N 9/02; C12N 15/53
[52] U.S. Cl. ...................... 435/189; 435/320.1; 514/44; 536/23.2
[58] Field of Search ................................ 435/189, 320.1; 514/44; 536/23.2

[56] References Cited

U.S. PATENT DOCUMENTS 5,246,847  9/1993  Hartman et al. ........................ 435/189
5,260,204  11/1993  Heckl et al. ............................. 435/189

FOREIGN PATENT DOCUMENTS 284105  9/1988  European Pat. Off. .
WO 92/08482  5/1992  WIPO .

OTHER PUBLICATIONS

Hsieh, Y. et al., "Probing the active site of human manganese superoxide dismutase: the role of glutamine 143," *Biochemistry*, 37:4731–4739, (1998).

Whittaker, M. et al., "Mutagenesis of a proton linkage pathway in *Escherichia coli* manganese superoxide dismutase," *Biochemistry*, 36:8923–8931 (1997).

Barra, D. et al. (1984) "The primary structure of human liver manganese superoxide dismutase", *J. Biol. Chem.* 259:12595–12601.

Beck, Y. et al. (1987) "Human Mn superoxide dismutase cDNA sequence" *Nucleic Acids Res.* 15(21): 9076.

Borgstahl, G.E.O. et al. (1992) "The structure of human mitochondrial manganese superoxide dismutase reveals a novel tetrameric interface of two 4–helix bundles" *Cell* 71:107–118.

Bull, C. et al. (1991) "Kinetic studies of superoxide dismutases: properties of the manganese–containing protein from *Thermus thermophilus*" *J. Am. Chem. Soc.* 113(11):4069–4076.

Fee, J.A. et al. (1976) "Direct evidence for manganese (III) binding to the manganosuperoxide dismutase of *Excherichia coli* B" *J. Biol. Chem.* 251:6157–6159.

Hsu, J.–L., et al. (1996) "Catalytic properties of human manganese superoxide dismutase" *J. Biol. Chem.* 271:17687–17691.

Holm, R.H. et al. (1996) "Structural and Functional Aspects of Metal Sites in Biology" *Chem. Rev.* 96:2239–2314.

Lah, M.S. et al. (1995) "Structure–function in *Escherichia coli* iron superoxide dismutase: comparisons with the manganese enzyme from *Thermus thermophilus*" *Biochemistry* 34:1646–1660.

Stephens, P.J. et al. (1996) "Protein Control of Redox Potentials of Iron–Sulfur Proteins" *Chem. Rev.* 96:2491–2513.

*Primary Examiner*—Charles L. Patterson, Jr.
*Attorney, Agent, or Firm*—Jane E. Remillard; Lahive & Cockfield, LLP

[57] ABSTRACT

Human manganese superoxide dismutase (hMn SOD) having catalytic activity which differs from natural hMn SOD is disclosed. The hMn SOD of the invention exhibits reduced or no product inhibition compared to natural hMn SOD, while preferably maintaining equal or improved catalytic activity. The hMn SOD of the invention can be used as an antioxidant to prevent or treat cytotoxicity resulting from oxidation.

14 Claims, 8 Drawing Sheets

Scheme 1

HUMAN MANGANESE SUPEROXIDE DISMUTASE PROTEINS

GOVERNMENT FUNDING

This invention was made with government support under grant GM54903 awarded by the NIH. The United States government has cetain rights in the invention.

BACKGROUND OF THE INVENTION

Oxidative metabolism in respiring cells generates highly reactive superoxide ($O_2^-$) radicals which cause cellular damage (see e.g., Pasquier et al. (1984) *Inflammation* 8:27–32). A group of metalloenzymes known as superoxide dismutases (SOD) help defend against such cellular damage by catalyzing the oxidation-reduction reaction $2O_2^- + 2H^+ \rightarrow H_2O_2 + O_2$, thus acting as antioxidants.

There are several known forms of SOD, both eukaryotic and prokaryotic. These forms include different metals, such as iron, manganese, copper and zinc. Eukaryotic cells, in particular, contain two forms of SOD. The first form is copper-zinc SOD (Cu/Zn SOD) which is found in the cytosol. The second form is manganese SOD (Mn SOD) which is found in the mitochondria and has also been detected in the cytosol of liver cells (see e.g., McCord et al. "Superoxide and Superoxide Dismutases," Academic Press, N.Y., 1977).

Evidence indicates that SOD may be clinically useful as an antioxidant in many clinical applications, such as protection against ischemia, chemotoxicity (e.g., from anticancer agents) and inflammation (see e.g., Oberley et al. (1979) *Cancer Res.* 39:1141–1149; Huber et al. (1980) *Clinics in Rheum Dis.* 6:465–498; and McCord et al. (1982) *Physiol. Pharma.* 60:1346–1352). Specifically, deficiency of human Mn SOD has been linked to the development of clinical rheumatoid arthritis (Pasquier et al., supra.). In addition, human Mn SOD has been suggested to protect against alcohol-induced liver damage (Del Villano et al. (1980) *Science* 207:991–993), and has been shown in vitro to protect human phagocytosing polymorphonuclear leukocytes from superoxide free radicals more effectively than bovine or porcine Cu/Zn SOD (McCord et al., supra.).

A full-length 196 amino acid sequence for human Mn SOD isolated from human liver cells has been published by Barra et al. (1984) *J. Biol. Chem.* 259:12595–12601. This sequence differs from the cloned full-length (mature) human Mn SOD amino acid sequences disclosed and claimed in each of U.S. Pat. No. 5,260,204 (Heckl et al.), and U.S. Pat. No. 5,246,847 (Hartman et al.). Specifically, the 196 amino acid sequence of Barra et al. contains a Glu residue instead of a Gln residue at positions 42, 88, 109 and 131. The 196 amino acid sequence of Barra et al. also differs in that it lacks amino acids Gly and Trp between positions 123 and 124 contained in the sequences of U.S. Pat. No. 5,260,204 (Heckl et al.), and U.S. Pat. No. 5,246,847 (Hartman et al.). Moreover, the cloned human Mn SOD amino acid sequence in U.S. Pat. No. 5,260,204 (Heckl et al.) differs from the cloned sequence in U.S. Pat. No. 5,246,847 (Hartman et al.) in that it lacks a Met residue at the N-terminus and contains Glu instead of Gln at residue 146. These differences in amino acid sequence between naturally occurring sequences may be due to the existence of naturally occurring polymorphic variants of human Mn SOD which differ in amino acid sequence due to allelic variation.

The enzymatic activity of natural (wild-type) human and bacterial Mn SOD exhibits a biphasic pattern in the decay of $O_2^-$ under conditions for which the ratio $[O_2^-]/[E]$ is greater than approximately 10, as observed by stopped-flow (Bull et al. (1991) *J. Am. Chem. Soc.* 113:4069–4076; McAdam et al. (1977) *Biochem. J.* 165:71–79) and pulse radiolysis (Hsu et al. (1996) *J. Biol. Chem.* 271:17687–17691). This biphasic pattern constitutes an initial burst of catalysis followed by a much slower zero-order rate of the disproportionation of superoxide, representing an inhibited phase. Therefore, while initially highly active upon binding its substrate, natural Mn SOD is rapidly inhibited by product hydrogen peroxide ($H_2O_2$), causing it to become substantially inactive.

Accordingly, it is an object of the present invention to provide novel Mn SOD proteins which exhibit reduced or no product inhibition compared to their naturally occurring counterparts, and therefore which act as more efficient antioxidants. It is a further object of the invention to provide Mn SOD proteins which exhibit reduced or no product inhibition compared to their naturally occurring counterparts, while maintaining the same or higher catalytic activity compared to their naturally occurring counterparts, and/or which are more stable than their naturally occurring counterparts. It is a further object of the invention to provide nucleic acids encoding Mn SOD proteins of the invention, as well as expression vectors capable of expressing Mn SOD proteins of the invention e.g., following transfection into a host cell (e.g., a bacterial or mammalian cell). It is a further object of the invention to provide methods of using Mn SOD proteins of the invention as therapeutic antioxidative agents to protect cells against damage caused by free oxygen radicals. These and other objects will be apparent from the following summary and description.

SUMMARY OF THE INVENTION

The present invention provides novel human manganese superoxide dismutase (hMn SOD) proteins having catalytic activity which differs from natural hMn SOD in that it exhibits reduced or no product inhibition compared to naturally occuring hMn SOD, or has greater activity than naturally occuring hMn SOD, or has both reduced product inhibition and greater activity than naturally occuring hMn SOD. In one embodiment, the proteins of the invention comprise an amino acid sequence which differs from the sequence shown in SEQ ID NO:2 by one or more amino acid substitutions, additions or deletions. Preferred amino acids for modification include those which are within or interactive with the active site of the protein. Suitable substitute amino acid residues include those which are conservative, are smaller, and/or are more capable of protein transfer during hMn SOD catalysis.

In a particular embodiment, the invention provides a hMn SOD protein comprising an amino acid sequence which differs from the amino acid sequence shown in SEQ ID NO:2 by one or more substitutions of an amino acid selected from the group consisting of His 26, His 30, Tyr 34, His 74, Gln 143, Asp 159, Trp 161 and His 163. A preferred substitution is the replacement of Gln 143 with an amino acid selected from the group consisting of Ala, Asn, His, Asp and Glu.

The present invention further provides a nucleic acid encoding a novel hMn SOD protein which exhibits reduced or no product inhibition compared to naturally occuring hMn SOD, or has greater activity than naturally occuring hMn SOD, or both. Also included within the scope of the invention are expression vectors containing a nucleic acid encoding a hMn SOD protein of the invention operably linked to a promoter which is preferably capable of driving transcription in a mammalian cell.

The present invention still further provides a method of protecting a cell from damage caused by superoxide radicals. The method comprises administering to the cell a novel hMn SOD protein of the invention or a nucleic acid encoding a novel hMn SOD protein of the invention. In a preferred embodiment, a nucleic acid encoding a novel hMn SOD protein is administered to a subject in a method of gene therapy to be expressed in respiring cells of the subject.

Accordingly, hMn SOD proteins and nucleic acids of the present invention can be used to treat subjects suffering from, or at risk of suffering from, cytotoxicity caused by superoxide radicals. As such, hMn SOD proteins and nucleic acids of the present invention are useful as antioxidants in the treatment of a variety disorders, including inflammation, reperfusion injury following ischemia, and cellular damage caused by chemotherapeutic agents.

DETAILED DESCRIPTION

Figure 1:
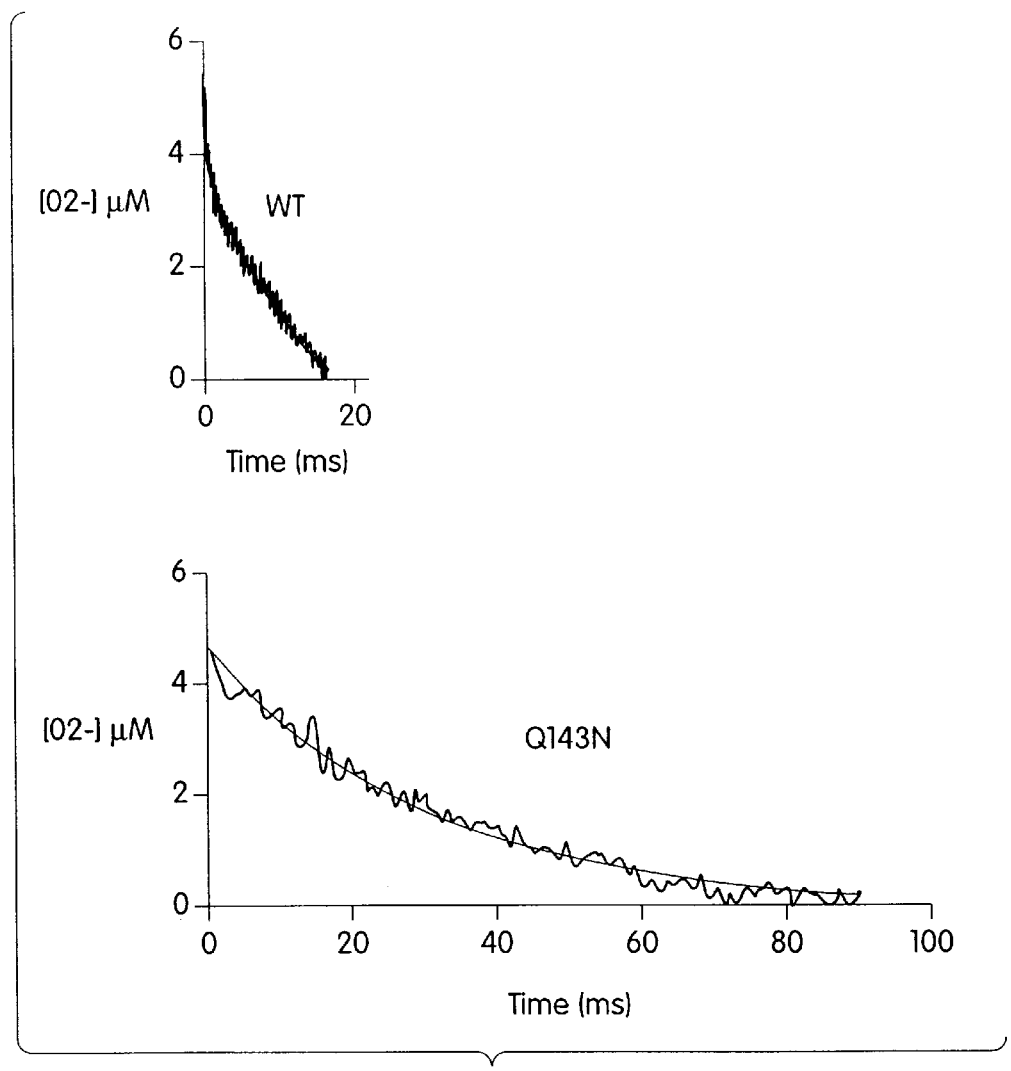
FIG. 1 shows a comparison of superoxide decay catalyzed by (top) wild-type hMn SOD and (bottom) Q143N hMn SOD as determined by pulse radiolysis. Data show the decrease in superoxide as determined from its absorbance at 250 nm ($\epsilon$=2000 $M^{-1}cm^{-1}$). The solutions contained 0.5 $\mu M$ wild-type MnSOD or 35 $\mu M$ Q143N hMnSOD and 50 $\mu M$ EDTA, 10 mM sodium formate, and 2.0 mM sodium pyrophosphate and pH 9.6 and 20° C. The solid line for Q143N hMnSOD is least-squares fit to a first-order process corresponding to $K_{cat}/K_m$=1×10$^6$ $M^{-1}s^{-1}$. The uncatalyzed dismutation rate was measured under these conditions and showed a change in $O_2^-$ concentration consistent with a bimolecular dismutation rate constant of 1800 $M^{-1}s^{-1}$.

The present invention is based on the discovery that human manganese superoxide dismutase (hMn SOD) can be modified to exhibit improved properties compared to naturally occurring hMn SOD.

In particular, as demonstrated in studies described herein, naturally occurring hMn SOD exhibits a biphasic pattern in the decay of superoxide ($O_2^-$) which consists of an initial burst of catalysis followed by a much slower zero-order rate of decay. This biphasic pattern is the result of inhibition of hMn SOD by its catalytic product, hydrogen peroxide ($H_2O_2$), and its related intermediate product, hydrogen peroxide anion ($HO_2^-$), as it carries out the oxidative reaction $2O_2^- + 2H^+ \rightarrow H_2O_2 + O_2$.

Accordingly, hMn SOD proteins of the present invention exhibit improved properties over naturally occurring hMn SOD in that they are less susceptible to product inhibition or exhibit no product inhibition at all. In a preferred embodiment, hMn SOD proteins of the invention exhibit reduced or no product inhibition while also having catalytic activity comparable to that of naturally occurring hMn SOD (e.g., at least about 75%, preferably at least about 85%, and most preferably at least about 90% or more of the catalytic activity of naturally occurring hMn SOD).

hMn SOD proteins of the present invention can also differ advantageously from their natural counterparts by having greater overall catalytic activity as measured by, for example, the steady state constant $K_{cat}/K_m$ for the decay of superoxide as a function of pH or substrate concentration. In a preferred embodiment of the invention, these advantages are combined in a hMn SOD protein which exhibits both reduced or no product inhibition compared to wild-type hMn SOD, while also maintaining or increasing the protein's catalytic activity and/or stability. In a particularly preferred embodiment, hMn SOD proteins of the invention are recombinantly produced either in vitro or in vivo (e.g., in methods of gene therapy) as therapeutic agents for the treatment of disorders involving superoxidation.

As used herein, the following terms and phrases shall have the following meanings:

The terms "novel", "modified" and "mutated" refer to a protein or nucleic acid which has been altered from its natural form in a manner which changes one or more properties of the protein or nucleic acid, such as its activity, function, pharmacological characteristics, structure, stability, or coding sequence, from the corresponding property possessed by the natural form. For example, the terms "novel", "modified" and "mutated" can include proteins and nucleic acids which have been altered from their natural forms by substitution, addition or deletion of one or more amino acids or nucleotides, or one or more other natural components of the protein or nucleic acid (e.g., components incorporated into the protein's secondary or tertiary structure, such as metal ions or sugar residues). The terms "novel", "modified" and "mutated" also include changes made to a protein or nucleic acid of the invention by reaction with biological or chemical agents, such as alkylating agents.

Figure 8:
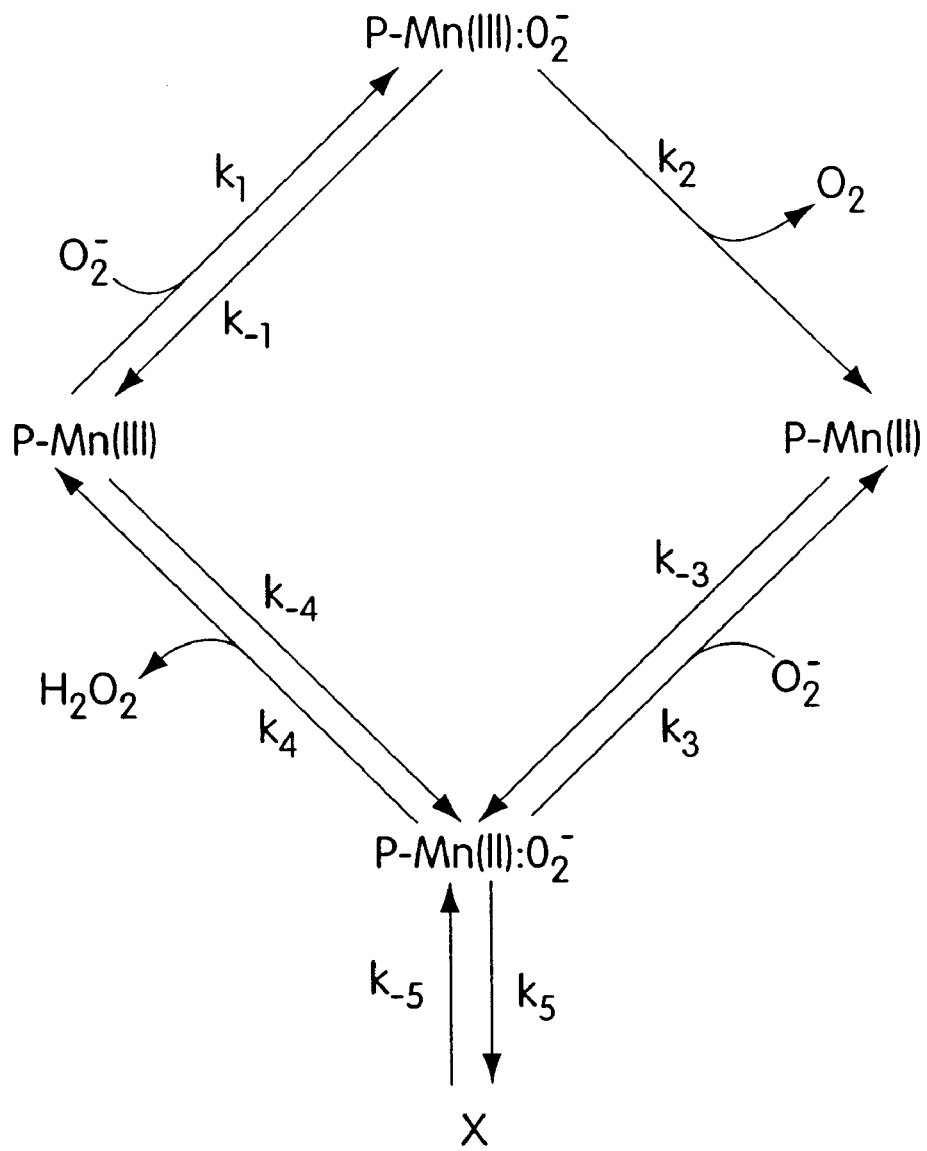
FIG. 8 is a schematic representation of the kinetic mechanism of wild-type hMnSOD.

The term "human manganese superoxide dismutase" or "hMn SOD" refers to any human Mn SOD protein capable of catalyzing the conversion of superoxide to hydrogen peroxide by the reaction $2O_2^- + 2H^+ \rightarrow H_2O_2 + O_2$ (see also FIG. 8). This includes all known human forms of the enzyme, such as that described by Beck et al. (1987) *Nucleic Acids Res.* 15:9076; Borgstahl et al. (1992) *Biochemistry* 35:4287–4297; Barra et al. (1984) *J. Biol. Chem.* 259:12595–12601; Hartman et al. (U.S. Pat. No. 5,246,847) and Heckl et al. (U.S. Pat. No. 5,260,204), as well as any isoforms of these proteins.

Human manganese superoxide dismutase (hMn SOD) is a homotetramer made up of four identical hMn SOD subunits. Each subunit has a reported molecular weight of approximately 22 kD (McCord et al. (1977)) and consists of a mature protein having 198 amino acids[1] and a leader sequence consisting of 24 amino acids, as shown in SEQ ID NO:2. The nucleic acid encoding each hMn SOD subunit comprises 666 nucleotides (coding region) followed by a 3' untranslated region which lacks the AATAAA polyadenylation signal. This nucleic acid is shown in SEQ ID NO: 1 and can be obtained in plasmid form from the American Type Culture Collection (Rockville, Md.) at accession number 59947.

[1] Barra et al. (1984), supra., characterize mature hMn SOD as having 196 amino acids, instead of 198 amino acids. However, all other reports to date characterize the mature protein as having 198 amino acids.

The terms "natural" or "naturally occuring" human manganese superoxide dismutase (hMn SOD) refer to a hMn SOD protein having the characteristics (e.g., structure, activity and function) of native (wild-type) hMn SOD (i.e., as found in nature).

The term "activity" or "catalytic activity" refers to the rate of superoxide decay catalyzed by hMn SOD represented by the reaction $2O_2^- + 2H^+ \rightarrow H_2O_2 + O_2$ as measured by any suitable enzymatic assay known in the art, including but not limited to those described herein (e.g., stopped-flow spectrophotometry and pulse radiolysis).

The term "product inhibition" refers to the reduction or complete inhibition of hMn SOD catalytic activity caused by the presence of one or more products or intermediary products generated from the decay of superoxide by hMn SOD.

hMn SOD proteins of the invention are made by modifying or mutating the structure or sequence of the naturally occuring protein in a manner which decreases its susceptibility to product inhibition, and/or increases its catalytic activity and/or stability. Generally, this is achieved by identifying and modifying residues which make up the active site of the enzyme, or residues which interact with active site residues, and which are therefore directly or indirectly involved in catalytic activity. The "active site" of the enzyme includes not only the five direct ligands (His 26, His 74, His 163, Asp 159 and one water molecule) which surround the active site metal (Mn) and hold it in place, but also several other residues which, upon folding of the protein, interact with the active site metal (e.g., by proton transfer or hydrogen boding) and form a positively charged pocket buried within the enzyme. Negatively charged superoxide substrate ($O_2^-$) binds to this pocket and is converted to product hydrogen peroxide through a complex series of reactions involving proton transfer and oxidative reduction catalyzed by the active site metal.

In addition to amino acid residues which form the active site of hMn SOD, there are other residues which, upon folding of the protein, interact with active site residues, for example, by properly orienting the active site residues toward the active site metal or by transferring protons to the active site residues. This can occur, for example, by way of electrostatic interactions (e.g., hydrogen bonds) and other intermolecular interactions.

Accordingly, appropriate residues for modification to produce a novel hMn SOD protein of the present invention can be selected in accordance with the guidelines provided herein on a basis of the relationship between the enzyme's activity and its overall tertiary structure (Borgstahl et al. (1992) *Cell* 71:107–118; Wagner et al. (1993) *Protein Sci.* 2:814–825) which is similar to that of bacterial Mn SOD proteins from *Bacillus stearothermophilus* (Parker et al. (1988) *J. Mol. Biol.* 199:649–661) and from *Thermus thermophilus* (Ludwig et al. (1991) *J. Mol. Biol.* 219:335–358), as observed by crystallography studies. Preferred residues which can be modified according to the present invention to affect the enzyme's activity, stability and/or susceptibility to product inhibition are selected from those which make up or interact with the active site, as previously described. Among these residues, those which contribute to, or are capable of, proton donation during catalysis and/or which are critical to the protein's activity are particularly preferred.

In one embodiment of the invention, preferred hMn SOD amino acid residues for modification are chosen from those residues which are (a) located near the active site metal (e.g., have side chains positioned close to the active site metal), (b) are directly or indirectly (e.g., through a hydrogen bond relay) involved in proton transfer to the active site metal, (c) are highly conserved among known Mn SOD proteins from various species, (d) have a pKa which is the same or similar to that required for hMn SOD catalysis (i.e., a pKa of approximately 9.0), (e) are involved in the reduction potential of the active site metal, and/or (f) contribute structurally to the compact nature of the active site. These residues can be determined by those skilled in the art having the benefit of the present disclosure by way of analyzing the known crystal structure and primary amino acid sequence of the enzyme as described by, for example, Borgstahl et al. (1992), supra. Particular examples of active site residues which can be modified according to the present invention include but are not limited to His 26, His 30, Tyr 34, His 74, Gln 143, Asp 159, Trp 161 and His 163.

Alternatively, residues involved in hMn SOD activity can be identified by comparing their pKa with the pKa of hMn SOD enzyme during catalysis. Amino acid residues which have the same or a similar pKa to hMn SOD during catalysis (i.e., a pKa of approximately 9.0) are likely involved in proton donation during catalysis and are thus likely involved in the enzyme's activity, making them good candidates for modification. One such residue, for example, is Tyr 34, located near the active site metal.

In one embodiment of the invention, modified hMn SOD active site residues are selected from the group consisting of Gln 143, Tyr 34 and His 30. These residues are located near the active site metal, are highly conserved, and are involved in a hydrogen bond relay which links the active site metal-bound hydroxyl (OH) group to ordered solvent by way of the following scheme:

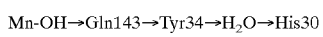

Mn-OH→Gln143→Tyr34→H$_2$O→His30

Thus, Gln 143, Tyr 34 and His 30 are all potentially involved in catalytic activity, product inhibition and/or stability of the enzyme, making them preferred targets for modification.

Once suitable amino acid residues of hMn SOD which are involved in the enzyme's activity and/or stability are selected in accordance with the guidelines provided above, these residues are modified in a manner which advantageously changes the protein's properties, for example, so that it acts as a more effective therapeutic agent, for example, when it is expressed in suitable cells of a subject or when produced ex vivo and then administered exogenously to the subject. Preferred modifications of the invention include those which reduce or eliminate the enzyme's product inhibition compared to naturally occuring hMnSOD, or which increase the enzyme's activity compared to naturally occuring hMn SOD, or which increase the enzyme's stability compared to naturally occuring hMn SOD, or which achieve all or a combination of these goals.

Suitable modifications of the invention include but are not limited to substitutions, additions and deletions of one or more hMn SOD amino acids selected as described above, as well as corresponding nucleotide substitutions, additions and deletions within the coding region of a nucleic acid encoding hMn SOD. Substitutions, additions and deletions such as those described herein can be made within any known hMn SOD protein sequence, such as that shown in SEQ ID NO:2. Accordingly, in one embodiment, the present invention provides a modified hMnSOD protein comprising an amino acid sequence which differs by one or more amino acid substitutions, additions or deletions from the amino acid sequence shown in SEQ ID NO:2, or the mature portion thereof, or the portion thereof which comprises the active site of the enzyme.

Other suitable modifications of the invention include substitutions, additions and deletions of other natural constituents of the protein which are preferably involved in enzymatic activity. For example, the active site metal (Mn) can be replaced with a different metal (e.g., Fe, Cu, or Zn) to increase enzymatic activity and/or decrease product inhibition. Still other suitable modifications include chemical modifications, such as reaction with alkylating agents capable of proton donation (e.g., bromo acetic acid).

In a preferred embodiment of the invention, appropriate hMn SOD amino acid residues identified according to the guidelines provided above are modified by substitution with one or more different amino acid residues. The selection of appropriate substitute amino acids will vary depending on the nature of the residue being replaced and its deduced function within the context of the natural enzyme. For example, appropriate choices will depend on factors such as the structure (e.g., size and shape (e.g., linear or cyclic)) of the residue, the electrostatic characteristics (e.g., charge and pKa) of the residue, the proton donating capability of the residue, and the location of the residue within the tertiary structure of the protein (e.g., its position in reference to the active site metal or within the active site pocket).

In one embodiment of the invention, one or more amino acids of hMn SOD are substituted with a conservative amino acid residue which reduces or eliminates the enzyme's susceptibility to product inhibition and/or increases the enzyme's activity and/or stability. "Conservative" amino acids include those which are similar with respect to one or more of the aforementioned characteristics.

In another embodiment of the invention, one or more amino acids of hMn SOD are substituted with a smaller residue (referring, e.g., either to the overall size of the residue or to the length of one or more of its side chains), preferably within or near the active site of the enzyme. For example, a residue which is located within the active site (e.g., near the metal) and which has a relatively long or bulky side chain compared to structurally similar residues can be replaced with one or more smaller residues which, for example, has a shorter side chain and which is therefore less prone to hinder the active site. In a particular embodiment of the invention, this is achieved by substituting bulky active site residues, such as Gln 143 or Tyr 34, with smaller residues, such as Asn, Ala or Gly.

Alternatively, a residue which is involved in the compact structure of the active site can be substituted with a smaller residue, or a residue which is not capable of interacting with neighboring residues in the same manner to "open up" (i.e., increase the size of) the active site as measured by, for example, the distance of the residue side chain from the active site metal. This can make it easier for substrate to bind and/or product (e.g., hydrogen peroxide or its intermediary anion) to leave the active site.

In a preferred embodiment, the invention provides a novel hMnSOD protein containing one or more substitutions of a Gln residue within the active site, such as Gln 143 (referring to the amino acid sequence shown in SEQ ID NO:2 or the corresponding residue in another mature hMn SOD protein). Preferred substitutions include replacement of Gln with a smaller residue (e.g., having a shorter side chain), such as Asn, Ala, Gly, His, Asp or Glu. In the case of Gln 143, substitution with a smaller amino acid, such as Asn or Ala, increases the distance of the residue from the active site metal and results in complete elimination of the enzyme's product inhibition. Accordingly, a particularly preferred hMn SOD protein of the invention comprises an amino acid sequence which differs from that shown in SEQ ID NO:2 in that Gln 143 is replaced by Asn, resulting in the modified protein shown in SEQ ID NO:3 (also referred to herein as "Q143N hMn SOD").

Other suitable substitutions e.g., to residues within or interactive with the active site of hMn SOD include replacement with residues which are conservative with respect to structure and/or charge, but which have greater proton donating capability. While all charged residues are potential proton donors, the pKa of the residue and whether or not its pKa is similar to that required for hMn SOD catalysis, will determine whether or not it participates in proton donation during catalysis. Thus, by replacing a charged active site residue with a different, and preferably structurally similar, charged residue which is more likely to donate protons at the pKa required for catalysis, activity and/or stability of the enzyme can be increased, and/or product inhibition can be decreased. Charged, proton donating residues include, for example, Lys, Arg, Cys, His and Tyr among others which are known to those of skill in the art.

Still other suitable modifications of the present invention include those which increase the stability of hMn SOD compared to natural hMn SOD as measured by, for example, thermal stability or shelf life. For example, the loss of certain hydrogen bonds within the active site can increase stability of the enzyme, as measured by $T_m$.

The foregoing particular hMn SOD modifications serve to illustrate the present invention. However many other modifications conforming to the goals and guidelines described herein will also be apparent to those of ordinary skill in the art based upon the present disclosure. Accordingly, these other modifications are included within the scope of the invention Moreover, hMn SOD modifications described herein can be made either alone or in combination within a single hMn SOD protein.

hMn SOD proteins of the invention can be prepared using a variety of techniques known in the art. For example, modifications can be made to the nucleotide sequence encoding naturally occuring hMn SOD so that it encodes a novel hMn SOD protein having one or more amino acid substitutions, additions or deletions from the wild-type sequence. This can be achieved by, for example, site-directed mutagenesis using a variety of known techniques and/or commercially available kits. In one method, site directed mutagenesis is performed using polymerase chain reaction (PCR) with oligonucleotide primers bearing one or more mutations (Ho et al. (1989) *Gene* 77: 51–59). Alternatively, whole, mutated proteins or genes which encode them can be synthesized (Hostomsky et al. (1989) *Biochem. Biophys. Res. Comm.* 161: 1056–1063). In addition, several commercial kits are available for performing site-directed mutagenesis, such as the Chameleon Double Stranded Site Directed Mutagenesis™ kit available from Stratagene Inc. or the Code 20 Cassette Mutagenesis™ kit available from New England Biolaboratories.

Alternatively, hMn SOD proteins of the invention can be prepared by reacting hMn SOD with chemical agents, such as an alkylating agents capable of proton donation, to achieve the desired change in the protein's properties. Human Mn SOD can also be modified by replacing its active site metal with a different metal, such as iron. This can be achieved, for example, by renaturing the protein in vitro with a compatible metal other than Mn.

hMn SOD proteins of the present invention can be produced recombinantly either in vitro in a suitable host cell (e.g., a bacterial cell, such as *E. coli*) or in vivo in a subject (e.g., a human). The full-length nucleotide sequence encoding naturally-occurring hMn SOD (with and without its 24 amino acid leader sequence which directs the protein to mitochondria where it is then cleaved off leaving the mature protein) is shown in SEQ ID NO: 1. This sequence is also published in references such as Beck et al. (1987) *Nucleic Acids Res.* 15:9076 and is available in plasmid form suitable for expression from the American Type Culture Collection (Rockville, Md.) at accession number 59947. Thus, to produce novel hMn SOD proteins of the invention, such as those described above, the nucleotide sequence encoding hMn SOD can be modified (i.e., the coding sequence changed at one or more codons) so that the amino acid modifications are incorporated into the expressed hMn SOD protein.

Accordingly, the present invention provides in another aspect a nucleic acid encoding a hMn SOD protein having catalytic activity which differs from natural hMn SOD, e.g., in that it exhibits reduced or no product inhibition compared to natural hMn SOD, or has greater activity and/or stability than natural hMn SOD, or exhibits these differences together. In one embodiment, the nucleic acid comprises a nucleotide sequence which encodes a protein which differs in amino acid sequence from natural hMn SOD (e.g., as shown in SEQ ID NO:2), or the mature portion thereof, or the portion thereof involved in activity of the enzyme (e.g., the portion comprising the active site), by the substitution, addition or deletion of one or more amino acids e.g., within or interactive with the active site of the protein.

The invention also features an expression vector comprising a nucleic acid encoding a hMn SOD protein of the present invention. Expression vectors which encode such hMn SOD proteins can be constructed using art-recognized techniques. Generally, the nucleotide sequence encoding the hMn SOD protein is contained in an appropriate vector (e.g., an expression vector), such as a plasmid, and is operably linked to appropriate genetic regulatory elements which are functional in the cell to be transformed. Such regulatory sequences include, for example, promoter sequences which drive transcription of the gene.

Preferred plasmids for expression of a hMn SOD protein of the invention include but are not limited to pCDNA 3.1 (Stratagene, Inc), pTrc99A (Pharmacia Corp.) and pCRII (Invitrogen Corp.). Preferred promoters include those appropriate for expression in mammalian (e.g., human) cells, such as SV40, CMV and actin promoters. In one embodiment, the promoter sequence used in the expression vector is the natural Mn SOD promoter which can be derived from, e.g., the human or rat Mn SOD gene.

Regulatory sequences required for gene expression, processing and secretion are art-recognized and can be selected to direct expression of a modified hMn SOD protein in an appropriate cell. Accordingly, the term "regulatory sequence", as used herein, includes promoters, enhancers and other expression control elements. Such regulatory sequences are known and discussed in Goeddel, *Gene expression Technology: Methods in Enzymology*, p. 185, Academic Press, San Diego, Calif. (1990).

Once a hMn SOD protein of the invention has been made, its characteristics can be determined and compared to the natural hMn SOD to ascertain differences in, e.g., susceptibility to product inhibition, catalytic activity, and/or thermostability. The assays for making such determinations are well known in the art.

For example, suitable assays for determining the activity of a hMn SOD protein of the invention and/or for measuring inhibition of the protein's activity by product peroxide, include stopped-flow spectrophotometry (Bull et al. (1991) *J. Am. Chem. Soc.* 113:4069–4076) and pulse radiolysis assays (Hsu et al. (1996) *J. Biol. Chem.* 271:17687–17691), both described in working examples below. In these assays, catalytic activity is measured and compared among different modified hMn SOD proteins of the invention and natural hMn SOD protein in terms of the ratio of steady state constants $K_{cat}/K_m$ for the decay of superoxide as a function of the concentration of pH or substrate $O_2^-$. Thus, using these assays, a decrease in product inhibition possessed by a modified hMn SOD protein of the invention compared to naturally occurring hMn SOD can be determined by a change in the characteristic biphasic pattern of superoxide ($O_2^-$) decay observed with natural hMn SOD (consisting of an initial burst of catalysis followed by a much slower zero-order rate of decay) toward a pattern which is closer to or representative of simple Michaelis-Menten kinetics with less or no evidence of cooperativity.

In addition to activity and product inhibition, hMn SOD proteins of the invention can be tested for increased stability compared to natural hMn SOD. This can be measured in a number of different art-recognized assays including, for example, differential scanning colorimetry (using, e.g., a Microcal-2 and a CSC Nano high sensitivity differential scanning calorimeter) to obtain denaturation profiles of the enzyme. Alternatively, a more simple assay involves merely heating the mutant hMn SOD proteins of the invention and wild-type hMn SOD proteins and comparing the temperature at which they denature and precipitate out of solution. hMn SOD proteins of the invention preferably have greater heat stability than natural hMn SOD making them easier to purify and less susceptible to decay.

hMn SOD proteins of the invention and related constructs, such as expression vectors encoding modified hMn SOD proteins, can be delivered to cells either in vivo or in vitro as a composition along with a pharmaceutically acceptable carrier or diluent. The term "pharmaceutically acceptable carrier or diluent" is intended to include any biologically compatible vehicle which does not significantly reduce the activity of the hMn SOD enzyme and which is physiologically tolerable to the patient. Such agents include a variety of solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

In a preferred embodiment of the invention, hMn SOD protein is expressed in vivo in a cell of a subject suffering from or susceptible to damage by superoxide. Once administered to the subject, a gene encoding a modified hMn SOD protein of the invention is taken up by cells (or can be targeted to particular cells) where it is generally expressed in the cell nucleus. If the subject is a mammalian subject (e.g., a human), the protein is expressed with its leader sequence and is directed out of the nucleus into mitochondria where it is processed and its signal peptide is cleaved off. The mature protein then becomes fully active within the mitochondria of the cell and acts as a more potent antioxidant than natural hMn SOD due to its decreased product inhibition and/or increased activity. The modified hMn SOD can also act in combination with natural Mn SOD in the cell to prevent damage from free oxygen radicals.

Several techniques for in vivo gene delivery are known in the art. Suitable methods include, for example, injection of naked DNA (U.S. Pat. No. 5,580,859) and/or targeted delivery of DNA to cells using, e.g., liposomal carriers or cell-specific ligands (U.S. Pat. No. 5,635,387). Particular cells which can be targeted for delivery and expression of modified hMn SOD include, for example, liver cells and neural cells.

Administration of a modified hMn SOD protein of the invention to a subject can be in any pharmacological form including a therapeutically active amount of a modified hMn SOD protein or nucleic acid alone or in combination with another therapeutic molecule. Administration of a therapeutically active amount of a therapeutic composition of the present invention is defined as an amount effective, at dosages and for periods of time necessary to achieve the desired result (e.g., antioxidation as measured by, e.g., an improvement in clinical symptoms, such as a decrease in inflammation etc). For example, a therapeutically active amount of a modified hMn SOD protein or nucleic acid may vary according to factors such as the disease state, age, sex, and weight of the individual. Dosage regimens may be adjusted to provide the optimum therapeutic response. For example, several divided doses may be administered daily or the dose may be proportionally reduced as indicated by the exigencies of the therapeutic situation.

Compositions containing hMn SOD proteins or nucleic acids encoding these proteins may be administered in a convenient manner such as by injection (subcutaneous, intravenous, intraarticular etc.), oral administration, inhalation, or transdermal application. Depending on the route of administration, the active compound may be coated in a material to protect the compound from the action of enzymes, acids and other natural conditions which may inactivate the compound. For example, a hMn SOD protein of the invention or related construct may be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27). Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating hMn SOD proteins of the invention or related constructs in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the particular individual to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Compositions containing hMn SOD proteins or nucleic acids of the invention should be administered to a subject for a sufficient time period to achieve the desired therapeutic or diagnostic result in the subject. The concentration of active compound in the drug composition will depend on absorption, inactivation, and other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Accordingly, the present invention further provides methods for protecting cells from oxidative damage using hMn SOD proteins or nucleic acids of the invention. These methods involve administering to cells a hMn SOD protein of the invention in a manner as described above, or transfecting cells either in vitro or in vivo with an expression vector encoding a hMn SOD protein of the invention. As effective and improved antioxidants (catalyzing the decay of free oxygen radicals) compared to natural hMn SOD, modified proteins of the invention can be used therapeutically in methods of preventing cytotoxicity resulting from the production of superoxide radicals in respiring cells.

In a particular embodiment of the invention, hMn SOD proteins of the invention (e.g., expressed in vivo or administered exogenously) are used to treat inflammation in a patient, or to treat reperfusion injury following ischemia. In another particular embodiment of the invention, modified proteins of the invention (e.g., expressed in vivo or administered exogenously) are used to treat or prevent cellular damage from chemotherapeutic agents. However, hMn SOD proteins of the invention can be used to treat or prevent any disorder, or the damaging effects of any agent, which causes the production of superoxide radicals in an individual (e.g., at levels higher than those found in the absence of the disorder or agent).

This invention is illustrated further by the following examples which should not be construed as further limiting the subject invention. The contents of all references and published patent applications cited throughout this application are hereby incorporated by reference.

EXAMPLES

Materials and Methods

PCR-based site-directed mutagenesis

The oligonucleotides GCATATGAA-GCACAGCCTCC (SEQ ID NO:4) and GGAGATCTCAGCATAACGATC (SEQ ID NO:5) were used as primers for PCR to amplify the hMnSOD cDNA (cDNA sequence reported by Beck et al. (1987). The plasmid pHMNSOD4 (ATCC#59947) which contains hMnSOD was subcloned into the TA cloning vector, pCRII (Invitrogen Corp.)

Four primers were designed and used for PCR-based site-directed mutagenesis to create the mutant Q143N hMn-SOD (replacing Gln 143 with Asn). These included a pair of oligonucleotides, primer 1 (5' GCAGCTTACTGTATTTG-CAG 3') (SEQ ID NO:6), and 2 (5' CCTTT-AAACACAGCCTCCCCG 3') (SEQ ID NO:7), which through PCR recreate the entire MnSOD coding region thus flanking the mutation. In addition two oligonucleotides, designated as primer 3 (5' GCTTGTCCAAATAACGATCCACTGC3') (SEQ ID NO:8) and 4 (5' AGTGGATCGTTATTTGGA-CAAGC 3') (SEQ ID NO:9) were prepared, whose sequences were complementary to each other and contained the mutation of interest.

Four primers were also designed and used for PCR-based site-directed mutagenesis to create the mutant Y34F hMn-SOD (replacing Tyr 43 with Phe). The first two of these primers (primers 1 and 2) were the same as oligonucleotide primers 1 and 2 described above. Primers 3 and 4 for Y34F were complementary to each other and contained the mutation of interest as follows: primer 3 (5' CCACGCGGCCT-TCGTTAACAACCTG 3') (SEQ ID NO: 10) and primer 4 (5' CAGGTTGTTAACGAAGGCCGCGTGG 3') (SEQ ID NO: 11).

In the case of each mutant, Q143N and Y34F, two separate PCR reactions were used to amplify the 5' portion (primers 1 and 4) and 3' half (primers 3 and 2) of the MnSOD cDNA. The PCR products from these two reactions were purified by electroelution and used as template DNA for the second round of PCR using primers 1 and 2. The Q143N and Y34F hMnSOD PCR products were each cloned into the TA-cloning vector (pCRII) and subsequently subcloned into the expression vector, pTrc99A (Pharmacia Corp.). The subcloning was accomplished by using the restriction sites, DraI and PstI, incorporated into primers 1 and 2, respectively. The DraI site which corresponds to the N-terminal portion of the protein was annealed to the NcoI site in pTrc99A recreating an ATG codon whereas the C-terminal end of the cDNA was annealed to the PstI of the vector. The mutations were verified by DNA sequencing along with the remainder of the coding sequence. Both mutant constructs expressed hMnSOD in the mutant Sod A/Sod B $E.$ $coli$ (strain QC774) as a mature protein tagged with an extra Met at the amino terminus. Culture conditions included additional supplementation by 5 mM $MnCL_2$. Yields of MnSOD mutant protein were on average 50 mg of protein per 50 g of bacterial pellet.

Purification of human Mn SOD

The mutant Q143N and Y34 F hMnSOD proteins were purified from $E.$ $coli$ using a combination of heat treatment (60° C.) and ion exchange chromatography (DE52 and CM52) according to the procedures of Beck et al. (1988). The purity of the resulting samples was determined on SDS-polyacrylamide gels which showed one intense band. The purified enzyme was dialyzed extensively against EDTA and a portion of the resulting protein was digested with nitric acid for manganese analysis using atomic absorption spectrometry (Perkin Elmer 5100PC). These measurements were used to determine the concentration of enzyme.

Pulse radiolysis

Experiments were carried out at the Center for Fast Kinetics Research at the University of Texas at Austin using a 4-Mev van der Graaff accelerator. A single high-dose electron pulse was used to generate superoxide radical anions from oxygen in acqueous solutions containing 10 mM sodium formate as hydroxyl radical scavenger (Schwartz, 1981) and 50 $\mu$M EDTA in addition to buffer and enzyme. All pulse radiolysis experiments were carried out at 20° C. The dismutation Of $O_2^-$ was followed spectrophotometrically from its absorbance at 250 nm ($\epsilon$=2000 $M^1cm^1$, Rabani and Nielson, 1969) with a path length of 2.5 cm. Progress curves for each set of 6 to 9 experiments were averaged. Exposure to ultraviolet radiation was minimized by opening a mechanical shutter a fraction of a second before each pulse.

Stopped-flow spectrophotometry

Experiments were based on the stabilization of $KO_2$ in aprotic solvent and the subsequent large dilution of this solution by an aqueous solution of enzyme in a stopped-flow apparatus, as described by McClune and Fee (1978). $KO_2$ was dissolved in a mixture of dimethyl sulfoxide and N,N-dimethyl sulfoxide (2:1 by volume; Aldrich, spectrophotometric grade) with solubility of $KO_2$ enhanced with 18-crown-6 (Valentine and Curtis, 1975). The stopped-flow spectrophotometer (Kinetic Instruments, Ann Arbor, Mich.) was capable of efficient mixing of this solution with an aqueous solution of enzyme in buffer with a dead time between 1.5 and 2.0 ms. One drive syringe (capacity 50 µl) contained the aprotic solution of $O_2$. This was diluted fifty-fold by the contents of a second syringe (capacity 2.5 ml) which contained enzyme, EDTA, and buffer. The decay of superoxide in initial velocity experiments and progress curves was monitored by its absorption at 250 to 300 nm. Stopped-flow experiments were carried out at 5° C. Four or more kinetic traces were averaged to reduce noise. Steady-state parameters were obtained by least-squares analysis of such data (Leatherbarrow (1987) "Enzfitter: a nonlinear regression data analysis program for the IBM PC" Elsevier BIOSOFT, Cambridge).

EXAMPLE 1 hMn SOD Mutant Q143N

The results of previous studies using stopped-flow (Bull et al., 1991; McAdam et al., 1977a,b) and pulse radiolysis (Hsu et al., 1996) indicated that bacterial and human MnSOD demonstrate a biphasic pattern in the decay of $O_2^-$ under conditions for which the ratio $[O_2]/[E]$ is greater than approximately 10. This biphasic pattern is an initial burst of catalysis followed by a much slower zero-order rate of the disproportionation of superoxide representing an inhibited phase.

In the present study, pulse radiolysis was used to measure the rapid initial burst of activity with wild-type hMnSOD before the phase of inhibition began, which was one or two milliseconds after initiating catalysis under the conditions of FIG. 1 (top). This region was not observable by stopped-flow due to the mixing times in the instrument. When observed by pulse radiolysis and stopped-flow under similar conditions, catalysis by Q143N MnSOD showed no inhibited region up to $[O_2]/[E]$ as great as 50, and was described throughout its entire decay by a single first-order process using up to 1.0 mM superoxide (shown under conditions of low substrate concentration in FIG. 1, bottom). The apparent lack of inhibition for Q143N MnSOD, even under a wide range of conditions, allowed the use of stopped-flow spectrophotometry to a greater extent than for wild-type since the uninhibited catalysis was measurable after the instrument's dead-time of 1.5 to 2.0 ms.

Figure 2:
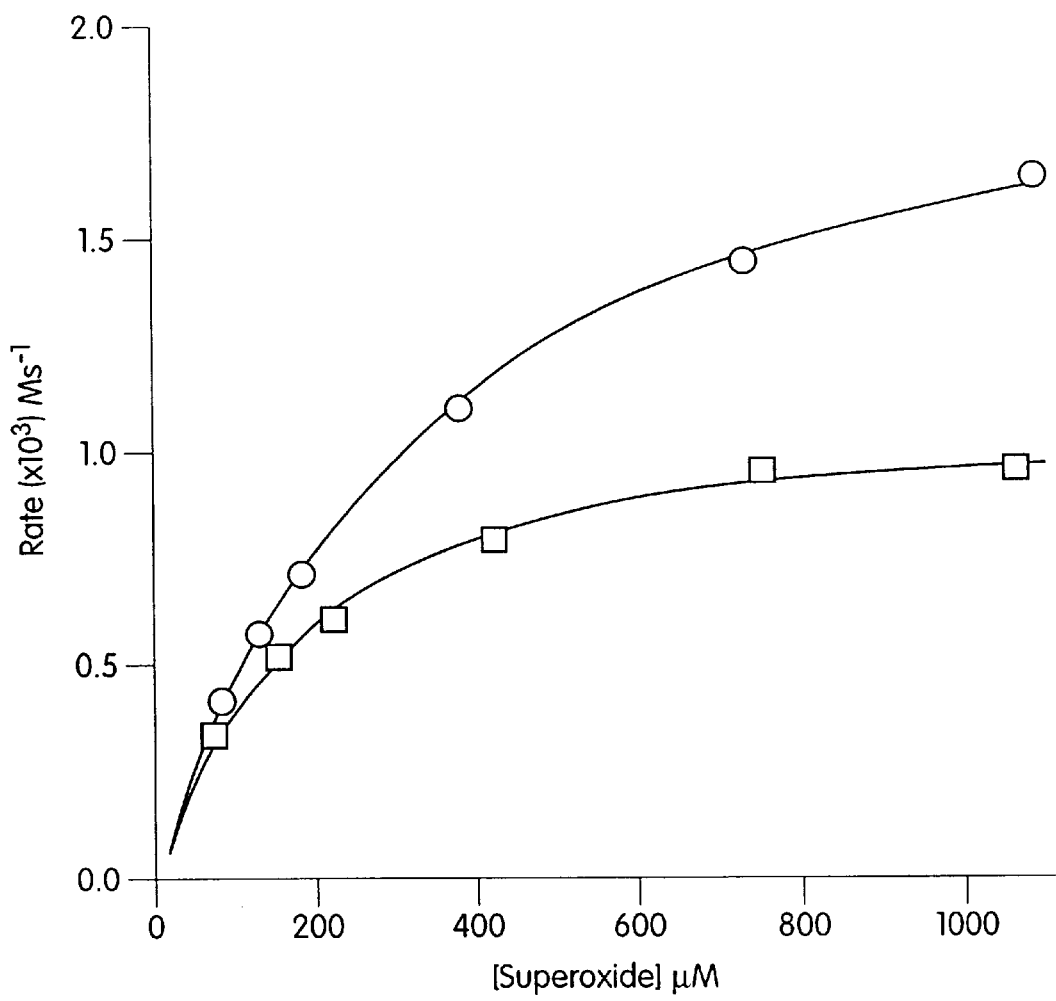
FIG. 2 shows the rate of superoxide decay in $H_2O$ (O) and in $D_2O$ (□) catalyzed by Q143N hMnSOD as a function of the concentration of substrate $O_2^-$ as measured by stopped-flow spectrophotometry. The concentration of Q143N hMn-SOD was 7.3 $\mu M$ in a solution containing 50 mM glycine buffer and 1 mM EDTA at pH 9.4 and 5° C. the solid line for $H_2O$ is a least-square fit of the Michaelis-Menten equation to the data resulting in $K_{cat}$=160 $s^{-1}$ and $K_{cat}/K_m$=8.5×10$^5$ $M^{-1}s^{-1}$.
Figure 3:
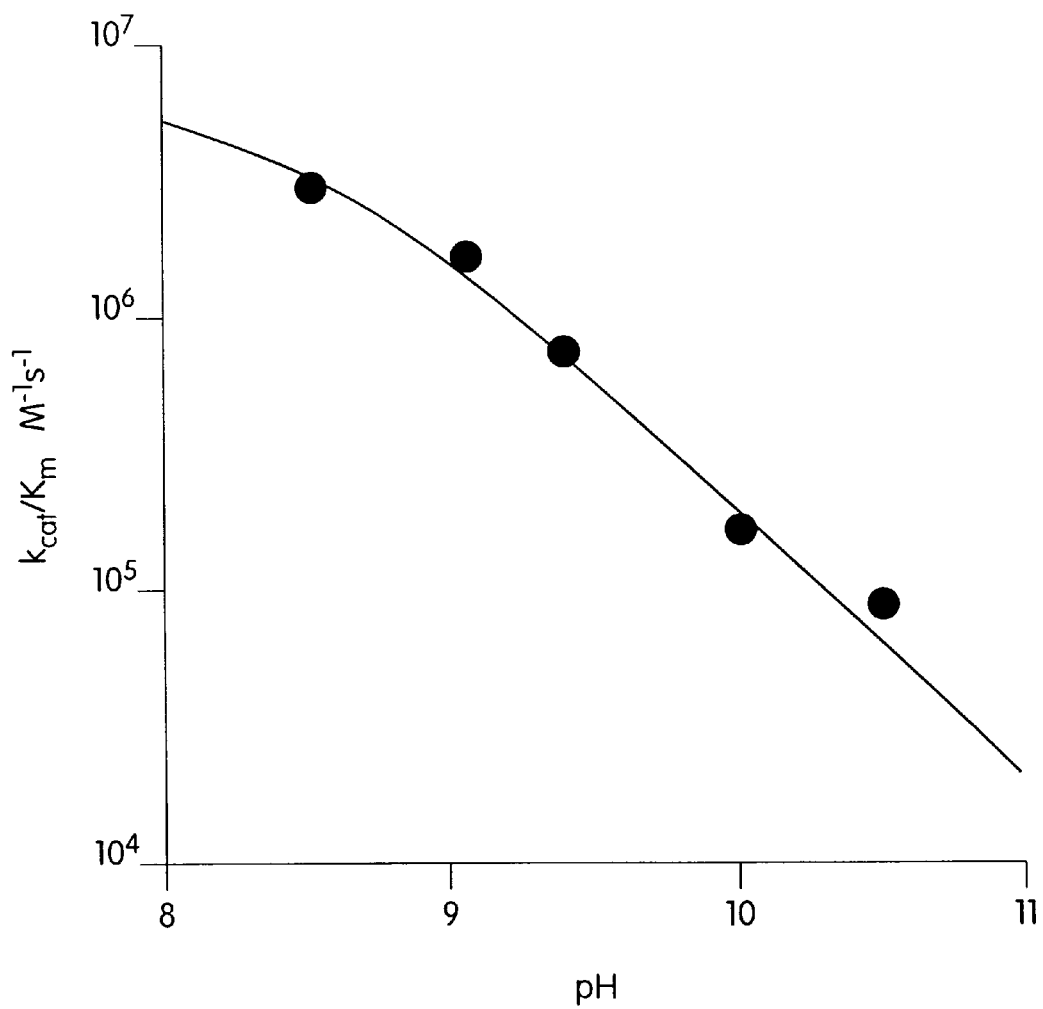
FIG. 3 shows the steady-state constant $K_{cat}/K_m$ for the decay of superoxide catalyzed by Q143N hMnSOD as a function of pH as determined by stopped-flow spectrophotometry at 5° C. A concentration of 50 mM of one of the following buffers was used: Taps (at pH 8.5); Ches (pH 9.0); glycine (pH 9.4); Caps (pH 10 and 10.5). The standard errors in individual points is less than 10%. The solid line is a least-square fit with $pK_a$=8.5±0.3 and a maximal value of $K_{cat}/K_m$=(7±3×10$^6$ $M^{-1}s^{-1}$).

As shown in FIG. 2, the initial velocities for the decay of $O_2^-$ catalyzed by Q143N MnSOD were adequately described by simple Michaelis-Menten kinetics. The pH profile for $K_{cat}/K_m$ over the range of pH 8.5 to 10.5 included a region of negative slope near unity, suggesting a dependence of the catalysis on the protonated form of a single group with pK, near or below 8.5 (FIG. 3). The value of $K_{cat}/K_m$ observed at pH 9.4 was $7 \times 10^5$ $M^{-1}s^{-1}$ at 5° C., about three orders of magnitude less than $K_{cat}/K_m$ for wild-type hMnSOD at pH 9.6 which is $8 \times 10^8$ $M^{-1}s^{-1}$ (Hsu et al. (1996) *J. Biol. Chem.* 271 :17687–17691; these data reported for 20° C.)

Figure 4:
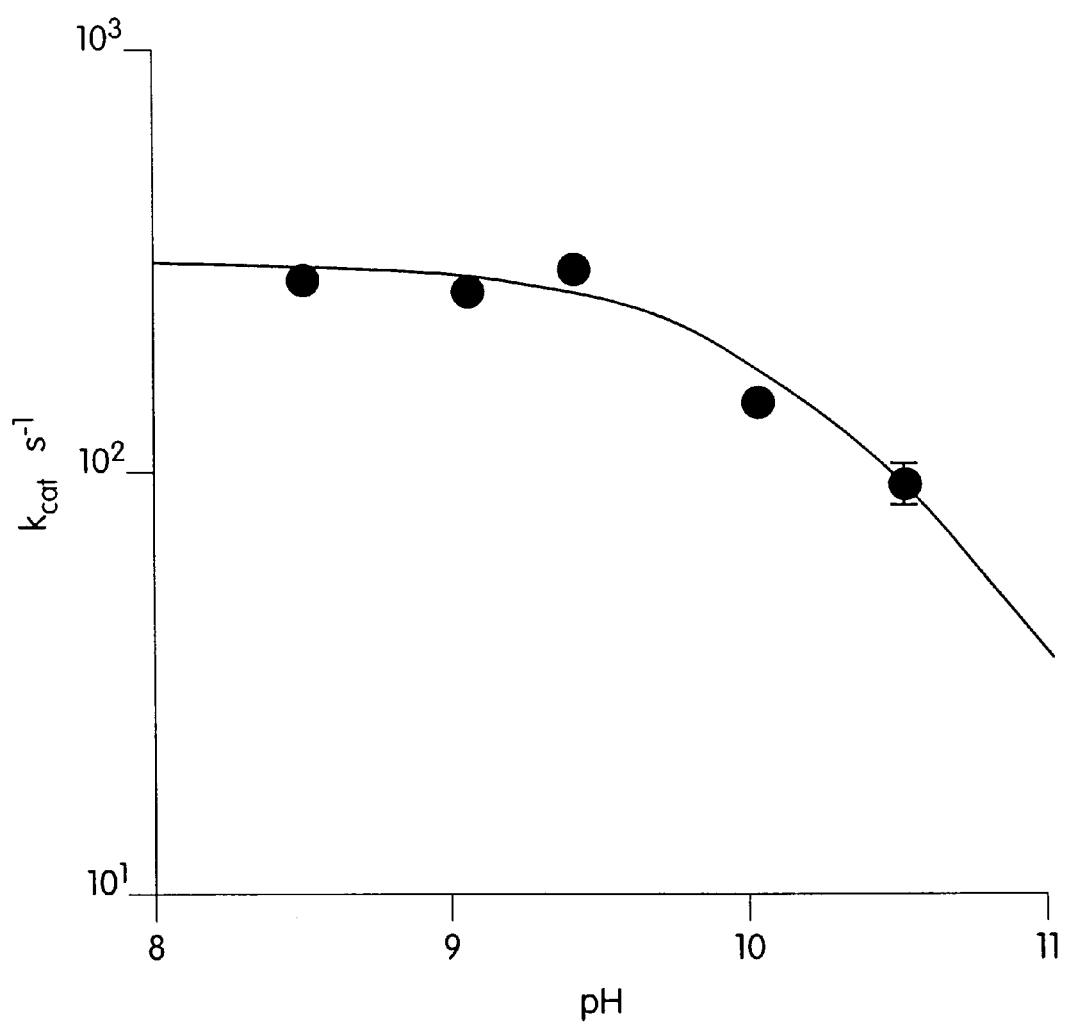
FIG. 4 shows the steady state constant $K_{cat}$ for the dismutation of superoxide catalyzed by Q143N hMnSOD as a function of pH as determined by stopped-flow spectrophotometry at 5° C. Conditions were the same as in FIG. 3. The standard error in individual points is less than 10%. The solid line is a least squares fit with $pK_a$=10.1±0.2 and a maximal value of $K_{cat}$=310±30.

The pH dependence of $K_{cat}$ for the decay of $O_2^-$ catalyzed by Q143N MnSOD suggested a $pK_a$ near 10 with a maximal value near 300 $s^{-1}$ (FIG. 4). This is also much less than the value of $k_{cat} = 4 \times 10^4$ $s^1$ observed for the wild-type hMn SOD at pH 9.6 (Hsu et al., 1996, supra.). As shown in FIG. 2, the solvent hydrogen isotope effects on the steady-state parameters of the reaction catalyzed by Q143N Mn SOD were measured at pH 9.4: $(k_{cat})_{H2O}/(k_{cat})_{D2O} = 1.9 \pm 0.1$; $(k_{cat})_{H2O}/(k_{cat})_{D2O} = 1.0 \pm 0.1$. Identical values were obtained when these isotope effects were measured at pH 10.0. This solvent hydrogen isotope effect on $K_{cat}$ is consistent with a rate-contributing proton transfer to the active site during maximal turnover. No enhancement of catalysis was observed upon increasing the concentration of the following buffers from 2 mM to 100 mM: glycine (at pH 9.6), ethanolamine (at pH 10.0).

Two other properties of Q143N hMn SOD were observed to be different from the wild-type enzyme. Whereas the wild-type hMn SOD was observed to have a broad visible absorption spectrum with a maximum at 480 nm assigned to Mn(III) (Hsu et al., 1996, supra) which is consistent with the MnSOD from *E. coli* (Fee et al. (1976) *J. Biol. Chem.* 251:6157–6159), the mutant Q143N Mn SOD had no detectable visible absorption. Atomic absorption verified that Q143N MnSOD contained manganese with a molar ratio of manganese to enzyme subunit near 0.7 as observed with the wild-type enzyme (Hsu et al., 1996, supra; Bull et al. (1991) *J. Am. Chem. Soc.* 113:4069–4076).

One very significant change caused by the conservative replacement Gln→Asn is the apparent shift of the reduction potential of manganese to a more positive value that renders Q143N MnSOD stable in the Mn(II) state under our solution conditions, while the wild-type MnSOD is clearly and predominantly in the Mn(III) state (FIG. 8). Support for this conclusion comes first from the absence of a visible absorption spectrum of the mutant Q143N, whereas wild-type hMn(III) SOD has a broad absorbance with a maximum at 480 nm (Hsu et al., 1996, supra). Reduction of bacterial MnSOD to the Mn(II) state was previously observed to abolish the visible spectrum (Fee et al., (1976) *J. Biol. Chem.* 251:6157–6159).

Several features in the mutant Q143N hMn SOD, such as an alteration in the hydrogen-bond scheme and ligand distances in the mutant, could influence the reduction potential of manganese as the active site, although it is difficult to quantitate their contributions (Stephens et al. (1996) *Chem. Rev.* 96:2491–2513).

Catalysis by Q143N hMnSOD showed no product inhibition even at $[O^-]/[E]$ as great as 50. Thus measurement of its catalysis was much more straightforward than with either wild-type (Bull et al., 1991, supra; Hsu et al, 1996, supra) or Y34F hMnSOD which become inhibited within one or two milliseconds under the experimental conditions described herein. The catalysis of superoxide decay by Q143N MnSOD followed simple Michaelis-Menten kinetics as shown in FIG. 2. Therefore, although the protein exists as a tetramer there appears to be no cooperativity.

Table 1 shows values of the steady-state parameters for the decay of superoxide catalyzed by natural hMnSOD and the two mutants, Q143N and Y34F, at pH 9.4.

TABLE 1

| Enzyme | $k_{cat}$ (ms$^{-1}$) | $k_{cat}/k_m$ ($\mu$M$^{-1}$s$^{-1}$) |
|---|---|---|
| wild-type MnSOD[a] | 40. | 800. |
| Y34F MnSOD[a] | 3.3 | 870 |
| Q143N MnSOD[b] | 0.3 | 0.82 |

[a]Data for wild-type (Hsu et al., 1996) and Y34F (Guan et al., 1997) measured at 20° C. and pH 9.6 by pulse radiolysis.
[b]Data obtained by stopped-flow spectrophotometry at 5° C. and pH 9.4.

It can be observed from the results shown in Table 1 that the replacement Gln 143 with Asn causes a decrease in the value of $K_{cat}/K_m$ for $O_2^-$ decay by three orders of magnitude compared with the wild-type at pH 9.6. $K_{cat}/k_m$ was strongly pH dependent in the range of pH 8.5 to 10.5 suggesting a $pK_a$ near or below 8.5 with a maximum near $7 \times 10^6$ M$^{-1}$s$^{-1}$ (FIG. 3). Thus, although both wild-type (Bull, et al., 1991, supra) and Y34F hMnSOD show values of $k_{cat}/k_m$ which are near $10^9$ M$^{-1}$s$^{-1}$ and are diffusion controlled, the mutant Q143N hMnSOD exhibits catalysis which is not diffusion controlled. It is unlikely that the replacement of Gln 143 with Asn has significantly impeded the access of superoxide to the active site; rather, this mutation has changed the rate-limiting step for $k_{cat}/k_m$ in Q143N to a step other than diffusion of superoxide. This is also consistent with the appearance of an apparent value of the $pK_a$ of $K_{cat}/K_m$ to a value near or below 8.5. This $pK_a$ is not observed in the wild-type hMn SOD (Hsu et al. (1996) J. Bop. Chem. 271:17687–17691). The cause of this apparent $pK_a$ is unclear, but because it occurs in the rate constant $K_{cat}/K_m$ describing catalysis at very low substrate concentration, it probably describes processes involved in the conversion of superoxide to oxygen and peroxide anion rather than rate-limiting proton transfers which are expected near maximal velocity when the enzyme is working near full capacity.

This view is strengthened by the solvent hydrogen isotope effect of unity on $K_{cat}/K_m$ for Q143N. The ratio $K_{cat}/K_m$ for E. coli Fe SOD shows a similar dependence on pH with an apparent $pK_a$ near 9.4 (Bull and Fee, 1985). This apparent $pK_a$ is believed to be caused by the addition of an hydroxide ligand to the metal in the ferric form; the $pK_a$ near 9 in the ferrous form is believed to be the ionization of Tyr 34 (Lah et al. (1995) Biochemistry 34:1646–1660). The reduced catalytic activity of Q143N hMn SOD and the enhanced stability of the Mn(II) state are related. The reduction potentials of the Cu/Zn, Fe and Mn SODs are all in the range of +0.25 V to +0.40 V to give maximum thermodynamic driving force in the oxidation and reduction cycles necessary for rapid catalysis of the disproportionation (Holm et al. (1996) Chem. Rev. 96:2239–2314). The alteration of hMn-SOD caused by the replacement of Gln with Asn has most likely shifted the reduction potential to a more positive value outside of this range and possibly altered the $pK_a$ of the water bound to manganese.

The catalytic turnover $K_{cat}$ for Q143N hMn SOD is less than that of the wild-type by about two orders of magnitude (Table 1), and there is some evidence for a weak pH dependence with an apparent $pK_a$, near 10 (FIG. 4). This rate constant represents the maximal rate of catalysis and the solvent hydrogen isotope effect of 1.9±0.2 suggests a contribution from proton transfer steps, the steps that protonate the peroxide anion at the active site and allow rapid dissociation of product (FIG. 8). Of course, the altered $pK_a$ of the manganese bound water, suggested by both the structural and kinetic results, could also affect the proton transfer rate.

Azide binding to superoxide dismutase offers clues to the binding of superoxide itself. In bacterial Mn SOD, azide is a ligand of the metal and hydrogen bonded to the hydroxyl of the Tyr 34 side chain (Lah et al., 1995, supra). This is consistent with the following observations based on the scheme shown in FIG. 8 which shows the mechanism used to describe catalysis by wild-type MnSOD (Bull et al., 1991, supra; Hsu et al., 1996, supra). As shown in below in Table 2 (containing values of the rate constants for catalysis by wild-type and Q143N hMn SOD obtained by fitting the scheme in FIG. 8 using KINSIM (Barshop et al., 1983) to the data for catalysis of the decay of superoxide), the fit of this scheme shows increased off-rates of substrate ($k_1$, $k_3$) for Q143N compared with wild-type. Thus, the results shown in Table 2 qualitatively represent trends in the catalytic pathway between wild type and mutants of hMn SOD.

TABLE 2

| Rate Constant | Wild-type MnSOD[a] | Q143N MnSOD[b] |
|---|---|---|
| $k_{-1}$ (M$^{-1}$s$^{-1}$) | $2 \times 10^9$ | $2 \times 10^9$ |
| $k_1$(s$^{-1}$) | $2 \times 10^4$ | $1.5 \times 10^6$ |
| $k_2$(s$^{-1}$) | $8 \times 10^4$ | 600 |
| $k_{-3}$(M$^{-1}$s$^{-1}$) | $2 \times 10^9$ | $2 \times 10^9$ |
| $k_3$(s$^{-1}$) | $2 \times 10^4$ | $1.5 \times 10^6$ |
| $k_{-4}$(s$^{-1}$) | $8 \times 10^4$ | 600 |
| $k_4$(M$^{-1}$s$^{-1}$) | $3 \times 10^2$ | $1 \times 10^3$ |
| $k_5$(s$^{-1}$) | $2 \times 10^4$ | $2 \times 10^4$ |
| $k_{-5}$(s$^{-1}$) | 130 | 200 |

[a]Fit was to pulse radiolysis data measured at 20° C. and pH 9.6 (Hsu et al., 1996).
[b]Fit was to stopped-flow data measured at 5° C. and pH 9.4 under the conditions of FIG. 3.

It is also possible that Gln 143 in wild-type MnSOD contributes to tight binding of product peroxide, and that in Q143N MnSOD interaction responsible for that binding is missing thus decreasing product inhibition in this mutant. However, a second explanation for the lack of product inhibition in this mutant is that the overall rate constant for peroxide formation at the active site may be much less than the rate constant for dissociation of peroxide from the enzyme. This suggestion is consistent with a fit of the kinetic data for Q143N hMnSOD to the scheme shown in FIG. 8 (Table 2) showing that catalysis by Q143N MnSOD can be explained using rate constants for the formation of the dead-end complex ($k_5$, $k_5$) that are the same as for the wild-type enzyme. That is, even though there is no evidence from these data of product inhibition in catalysis by Q143N hMnSOD, this is not necessarily due to a weaker binding affinity of the inhibiting form of peroxide at the active site.

Overall, the results observed from this experiment, demonstrate that (a) Gln 143 contributes to catalytic efficiency in Mn SOD but is not essential for catalysis; (2) Q143N showed no product inhibition when compared with wild-type which appears to be inhibited by product peroxide; (3) Gln 143 in Mn SOD has a substantial role in maintaining a reduction potential favorable for the oxidation and reduction cycles in the catalytic disproportionation of superoxide. With this residue replaced by Asn, the Michaelis-Menten parameters for catalysis are very significantly comprised by two to three orders of magnitude; (4) catalysis by Q143N Mn SOD obeys simple Michaelis-Menten kinetics showing that this mutant does not exhibit cooperativity in catalysis; (5) a solvent hydrogen isotope effect on $k_{cat}$ for Q143N hMn SOD suggests that the pathway for maximal velocity contains rate-contributing proton transfers to form product hydroperoxide anion or hydrogen peroxide. The replacement Gln 143 with Asn alters the hydrogen bonding scheme in the active site that may affect the delivery of protons to product peroxide; (6) catalysis by neither the wild-type nor the Q143N hMn SOD proteins studied are susceptible to enhancement by up to 100 mM of certain buffers in solution.

EXAMPLE 2 hMn SOD Mutant Y34F

In native hMn SOD, the hydroxyl group of Tyr 34 forms a hydrogen bond to the amide moiety of Gln 143 which is absent in the mutant structure due to the missing hydroxyl group. Thus, the single most significant structural change in the Y34F hMn SOD mutant compared to the wild-type enzyme is likely the breaking of the Tyr34-Gln143-$H_2O$-Mn hydrogen bonding chain.

Figure 5:
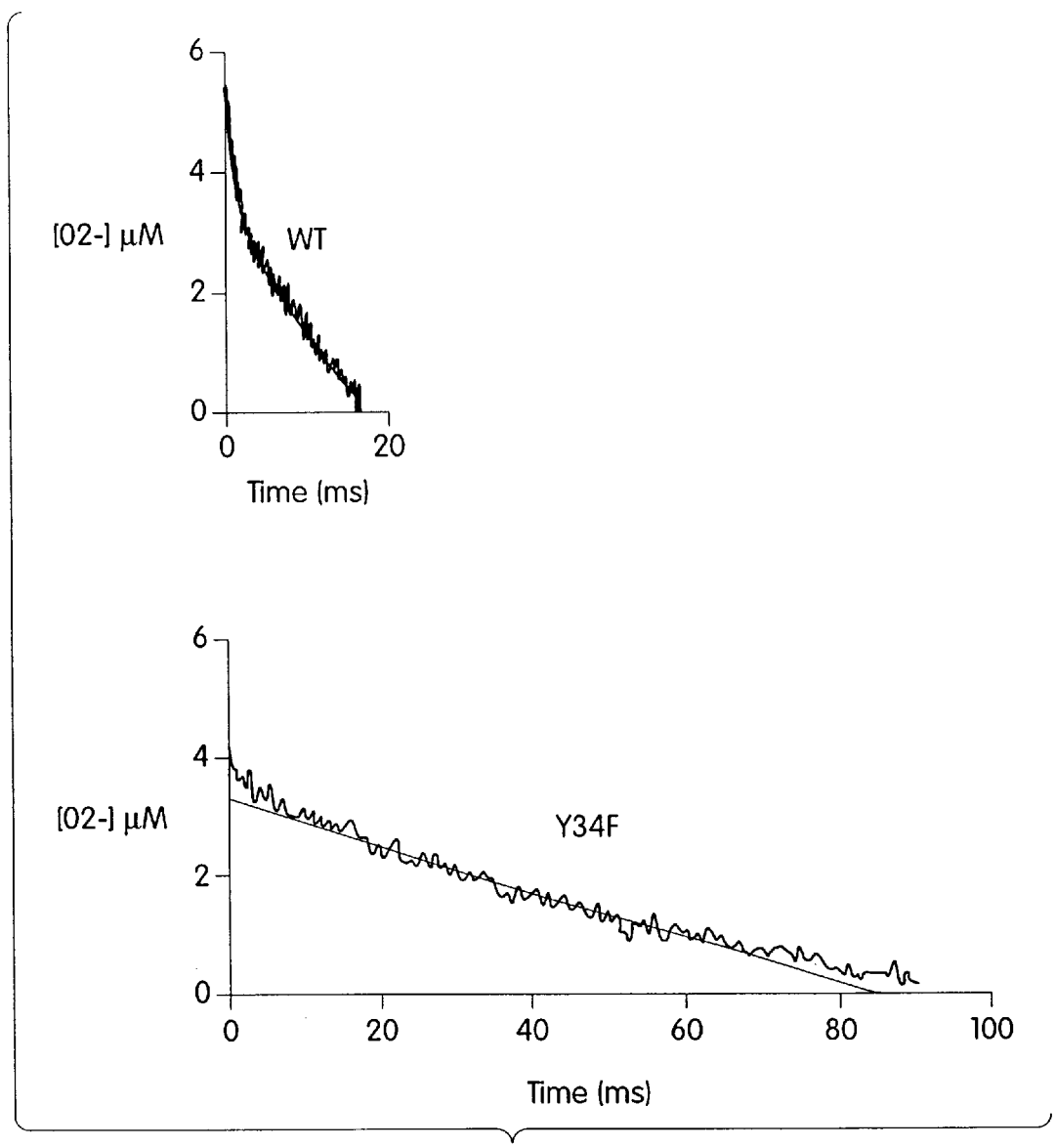
FIG. 5 shows a comparison of superoxide decay catalyzed by (top) wild-type hMnSOD and (bottom) Y34F hMnSOD as determined by pulse radiolysis. Data show the decrease in superoxide as determined from its absorbance at 250 nm ($\epsilon$=2000 $M^{-1}cm^{-1}$). The solutions contained 0.5 $\mu M$ wild-type hMnSOD or 0.5 $\mu M$ Y34F hMnSOD, 50 $\mu M$ EDTA, 10 mM sodium formate, and 2.0 mM sodium pyrophosphate at pH 9.6 and 20° C.

The general features of catalysis by Y34F hMn SOD are qualitatively similar to those of catalysis by wild-type hMn-SOD; there is an initial burst of activity followed by a region of much slower zero-order decay of superoxide (FIG. 5). The initial burst was evident in the first millisecond of catalysis and detected using pulse radiolysis. The zero-order region is interpreted for both *T. thermophilus* MnSOD (Bull et al., 1991, supra) and hMn SOD (Hsu et al., 1996, supra) as a region of inhibition caused most likely by the binding of product peroxide to MnSOD. The zero-order rate constant in this inhibited region for the Y34F mutant is smaller by about four-fold than that of the wild-type hMnSOD under comparable conditions suggesting that the extent of inhibition was greater for the mutant.

This conclusion was supported by the smaller size of the initial burst of activity catalyzed by Y34F MnSOD compared to the wild-type (FIG. 5). The amplitude of this burst represents catalytic decay of superoxide before the onset of the zero-order region of inhibition. The magnitude of this burst (in $\mu$M of $O_2^-$) as a function of enzyme concentration (in $\mu$M) had a slope of approximately 2, indicating that superoxide consumed in this initial burst is not stoichiometric with enzyme concentration and that multiple turnovers occur before the enzyme becomes inhibited. The slope of a similar plot for the wild-type hMn SOD under comparable conditions is 12, indicating that the wild-type enzyme is less inhibited and undergoes more catalytic cycles before inhibition than does Y34F MnSOD. In the wild-type hMnSOD this region of zero-order catalysis has a solvent hydrogen isotope effect from 2.2 to 3.1 depending on conditions, indicating a role for proton transfer in the steps by which the product is released from the inhibited enzyme (Hsu et al., 1996, supra). No enhancement of this zero-order region of the catalysis by either wild type or Y34F was observed upon increasing the concentration of the following buffers from 2 mM to 100 mM: glycine (at pH 9.6), ethanolamine (pH 10.0), carbonate (pH 10.3). Hence, this product inhibition cannot be overcome by donation of protons from these buffers in isolation.

Figure 6:
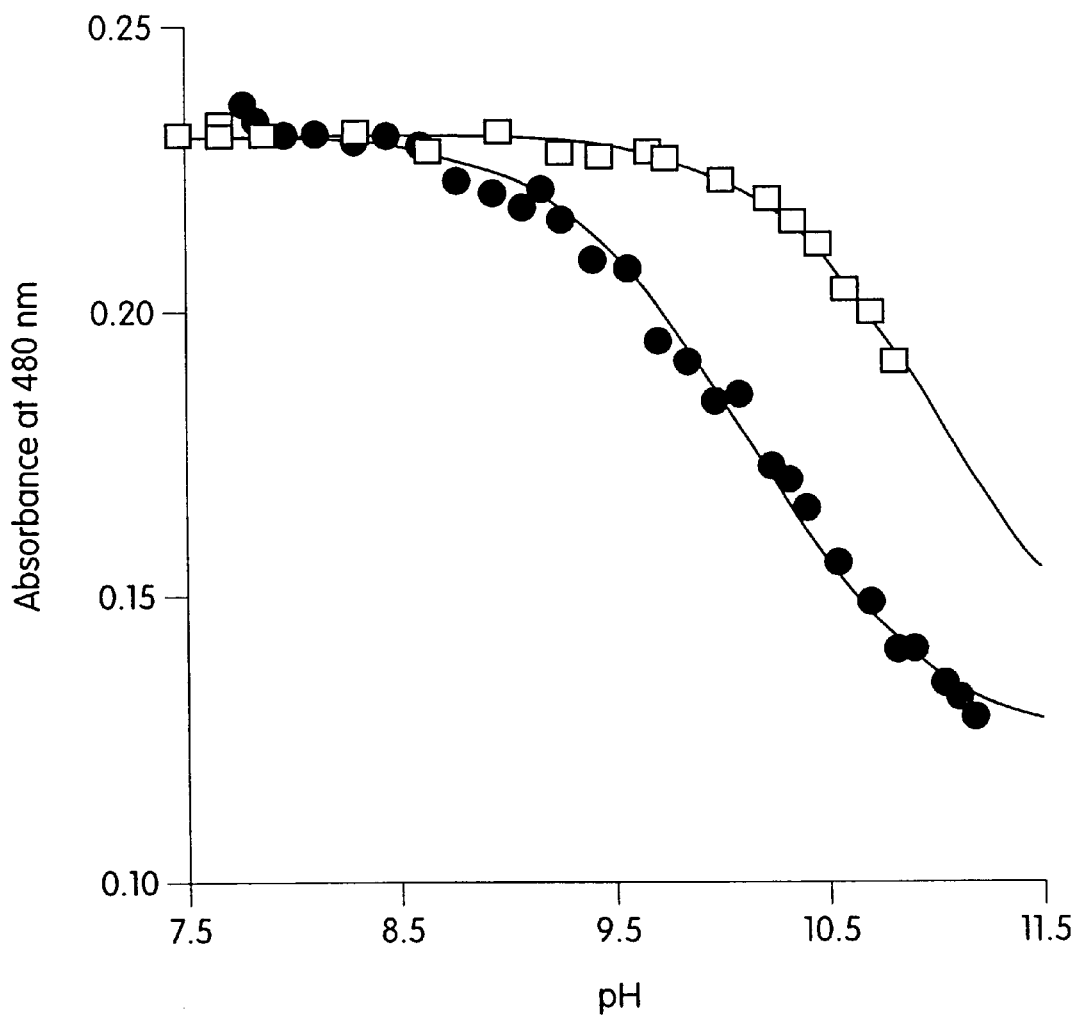
FIG. 6 shows the absorbance at 480 nm as a function of pH for Y34F hMn SOD (□) and the wild-type human MnSOD (O) at 20° C. The solid line for wild-type is a fit to a single ionization with a $pK_a$ of 10.1±0.1; for Y34F hMnSOD the value is $pK_a$=11.1±0.1.

The visible absorption spectrum of Y34F hMn SOD displayed a maximum at 480 nm with a shoulder at 600 nm, similar to published spectra of the wild-type enzyme (Beck et al., 1988, supra; Bull et al., 1991, supra; Hsu et al., 1996, supra). The pH dependence of this absorbance for Y34F hMn SOD can be described by a single ionization with $pK_a$ near 11; for the wild-type enzyme this $pK_a$ was closer to 10 (FIG. 6). There is evidence of enzyme denaturation above pH 11. An ionization of $pK_a$ near 9 is observed for wild-type FeSOD describing the pH dependence of $K_m$ and the binding of azide, among other properties (Bull and Fee, 1985). This $pK_a$ is believed to be caused by the addition of an hydroxide ligand to the metal in the ferric form. Crystal structure results indicated that the replacement Tyr 34 with Phe destroys the hydrogen bonding network involving this residue, Gln 143 and the metal-bound water. This is consistent with a destabilization of metal-bound hydroxide and hence an increase in the $pK_a$ and lower activity for Y34F.

Figure 7:
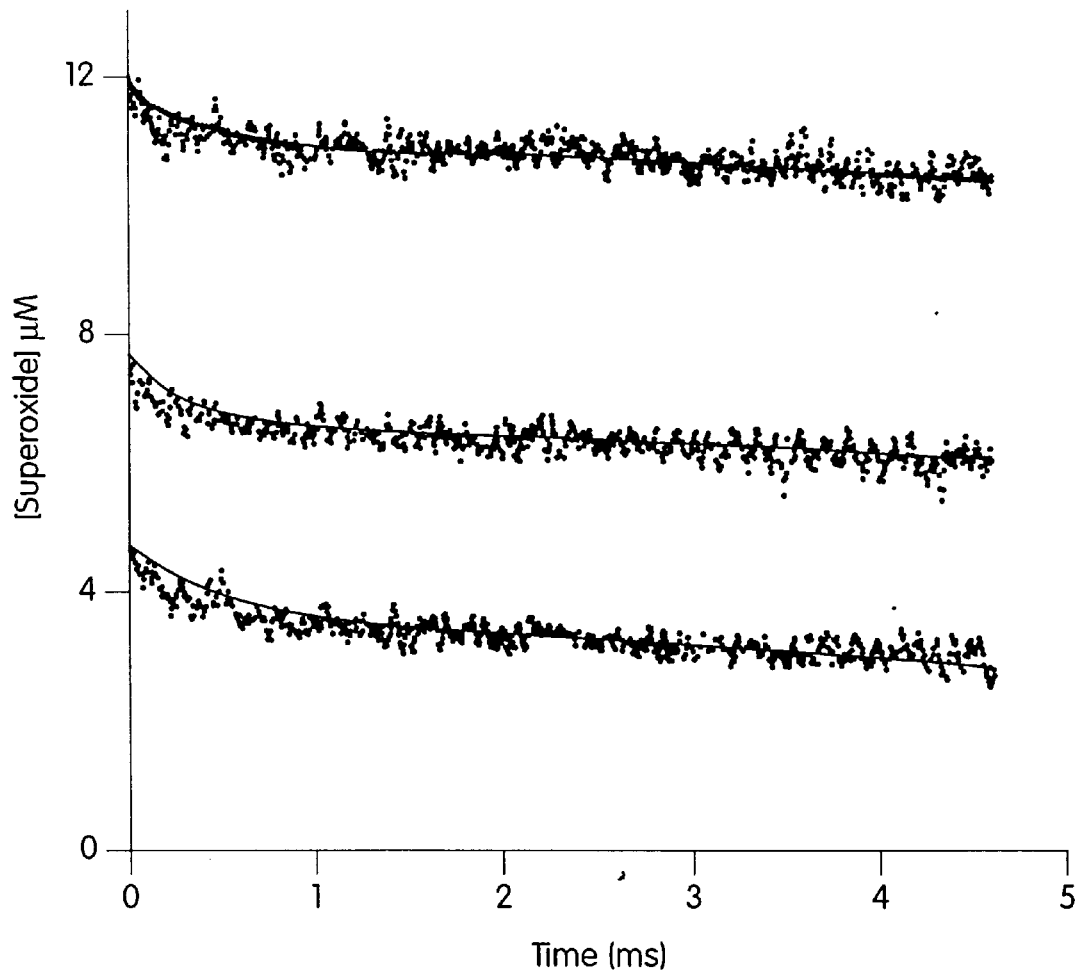
FIG. 7 shows superoxide decay catalyzed by Y34F hMn SOD as determined by pulse radiolysis. Data show the decrease in superoxide determined from its absorbance at 250 nm ($\epsilon$=2000 $M^{-1}cm^{-1}$). All solutions contained 0.5 $\mu M$ Y34F MnSOD, 50 $\mu M$ EDTA, 10 mM sodium formate, and 2.0 mM sodium pyrophosphate at pH 9.6 and 20° C. Traces from the top of the figure down contained 12 $\mu M$, 7.9 $\mu M$, and 4.9 $\mu M$ as initial concentrations of superoxide. The calculated lines shown in the figure are kinetic simulations (KINSIM), determined with the rate constants given in Table 3. The uncatalyzed dismutation rate was measured under these conditions and showed in change in $O_2^-$ concentration consistent with a bimolecular rate constant of 1800 $M^{-1}s^{-1}$.

The kinetic mechanism of FIG. 8 used to describe the wild-type MnSOD can also describe catalysis by Y34F Mn SOD (FIG. 7), as shown by pulse radiolysis. The fit was obtained using KINSIM (Barshop et al., 1983), and the rate constants for Y34F MnSOD obtained in this manner are shown below in Table 3 where they are compared with the constants found for the wild-type hMnSOD under comparable conditions. In this stimulation, the breakdown of the enzyme-substrate complex for enzyme in the reduced state, represented by $k_3$ in the scheme of FIG. 8, is much slower for Y34F compared with wild-type, whereas the values of $k_3$ are the same for both enzymes. This indicates a longer lifetime for this complex and hence a greater probability it will form the inhibited complex, which is confirmed by simulations of the catalysis using the data of Table 3 and KINSIM. The rate constants in Y34F for actual formation of the dead-end complex itself, $k_5$ and $k_5$ are quite similar to those for wild-type. Hence, the mutation of Tyr 34 to Phe may be altering the inherent catalysis of superoxide decay, and not the steps by which the inhibited complex is formed.

TABLE 3

| Rate constant | wild-type MnSOD[a] | Y34F MnSOD[a] |
|---|---|---|
| $k_1(M^{-1}s^{-1})$ | $2 \times 10^9$ | $2 \times 10^9$ |
| $k_1(s^{-1})$ | $2 \times 10^4$ | $1 \times 10^3$ |
| $k_2(s^{-1})$ | $8 \times 10^4$ | $5 \times 10^3$ |
| $k_3(M^{-1}s^{-1})$ | $2 \times 10^9$ | $2 \times 10^9$ |
| $k_3(s^{-1})$ | $2 \times 10^4$ | $1 \times 10^3$ |
| $k_4(s^{-1})$ | $8 \times 10^4$ | $1 \times 10^4$ |
| $k_4(M^{-1}s^{-1})$ | $2 \times 10^3$ | $1 \times 10^3$ |
| $k_5(s^{-1})$ | $2 \times 10^4$ | $2 \times 10^4$ |
| $k_5(s^{-1})$ | 130 | 200 |
| $k_7(M^{-1}s^{-1})$ | 2000 | 2000 |

[a]Fit was to pulse radiolysis data measured at 20° C. and pH 9.6 under the conditions of FIG. 8. The data for wild-type MnSOD is from Hsu et al. (1996).

As shown in Table 1, the value of $K_{cat}$ for Y34F is about ten-fold less than in wild-type, while the ratio $K_{cat}/K_m$ is nearly identical for the two forms of Mn SOD near $10^9$ $M^{-1}s^{-1}$, a value close to the diffusion-controlled limit. These values were obtained using the data of Table 3 and eqs 5–9 of Bull et al. (1991), supra. Thus at low concentrations of superoxide compared with $k_m$ (50 $\mu$M and 4 $\mu$M for wild-type and Y34F, respectively), the catalysis by these two enzymes is identical, but near substrate saturation the mutant Y34F Mn SOD is slower by ten-fold. This is consistent with a role for Tyr 34 in proton transfer, since it is at higher substrate concentrations that the enzyme needs rapid proton transfer to the active site and the maximal velocity of catalysis is expected to be proton transfer dependent in analogy with FeSOD (Bull and Fee, 1985). Tyr 34 itself may be the proton donor required to dissociate hydrogen peroxide or the hydroperoxide anion $HO_2^-$.

Overall, the results observed from this experiment, demonstrate that (1) the side chain hydroxyl of the conserved residue Tyr 34 in MnSOD contributes to catalytic efficiency in MnSOD but is not essential for normal cellular superoxide concentrations; (2) the replacement Tyr 34 with Phe does not affect the diffusion-controlled steady-state constant $K_{cat}/K_m$ which has a value near $10^9$ $M^{-1}s^{-1}$ for both wild-type and Y34F human MnSOD; (3) the replacement of Tyr 34 with Phe affects the rate of maximal catalysis $K_{cat}$, reducing by about ten-fold the steps that determine $K_{cat}$. This and the absence of the hydrogen-bonding scheme at the active site caused by the replacement of Tyr 34 with Phe suggests that Tyr 34 is a proton donor or is involved indirectly by its hydrogen bonded network to other residues and solvent for proton transfer; (4) the mutant Y34F shows enhanced product inhibition when compared with wild type. This may be related to decreased proton transfer capability in the active site of the Y34F mutant; and (5) catalysis in the substrate inhibited region by both Y34F or the wild type was not susceptible to enhancement by even up to 100 mM of buffer in solution, indicating that protonation from certain buffers in solution is not capable of enhancing the release of the inhibiting bound peroxide ion as expected from the structurally sequestered nature of the MnSOD active site.

References

Barshop, B. A., Wrenn, R. F., and Frieden, C. (1983) *Anal. Biochem.* 130:134–145.

Beck, Y., Oren, R., Amit, B., Levanon, A., Gorecki, M., and Hartman, J. R. (1987) *Nucleic Acids Res.* 15:9076.

Beck, B. A., Bartfield, D., Yavin, Z., Levanon, A., Gorecki, M., and Hartman, J. R. (1988) *Biotechnology* 6:930–935.

Bernstein, F. C., Koetzle, T. F., Williams, G. J. B., Meyer, E. F., Brice, M. D., Rodgers, J. R., Kennard, O., Shimanouchi, T. & Tasumi, M. (1977) *J. Mol. Biol.* 112, 535–542.

Borgstahl, G. E. O., Parge, H. E., Hickey, M. J., Beyer, W. F., Hallewell, R. A., and Tainer, J. A. (1992) *Cell*, 71:107–118.

Borgstahl, G. E. O., Parge, H. E., Hickey, M. J., Beyer, W. F., Hallewell, R. A., and Tainer, J. A. (1996) *Biochemistry* 35:4287–4297.

Brünger, A. T., Kuriyan, J. and Karplus, M. (1987) *Science* 235:458–460.

Bull, C., Niederhoffer, E. C., Yoshida, T., and Fee, J. A. (1991) *J. Am. Chem. Soc.* 113:4069–4076.

Bull, C. and Fee, J. A. 1985) *J. Am. Chem. Soc.* 107:3295–3304.

Fee, J. A., Shapiro, E. R., and Moss, T. H. (1976) *J. Biol. Chem.* 251:6157–6159.

Getzoff, E. D., Cabelli, D. E., Fisher, C. L., Parge, H. E., Viezzoli, M. S., Banci, L., Hallewell, R. A. (1992) *Nature* 358:347–351.

Guan, Y., Hickey, M. J., Borgstahl, G. E. O., Hallewell, R. A., Lepock, J. R., O'Connor, D., Hsieh, Y., Nick, H. S., Silverman, D. N., and Tainer, J. A. (1997) *Biochemistry*, submitted.

Holm, R. H., Kenepohl, P., and Solomon, E. I. (1996) *Chem. Rev.* 96:2239–2314.

Hsu, J. -L., Hsieh, Y., Tu, C. K., O'Connor, D., Nick, H. S., and Silverman, D. N. (1996) *J. Biol. Chem.* 271:17687–17691.

Jiang, J. -S. and Brünger, A. T. (1994) *J. Mol. Biol.* 243:100–115.

Lah, M. S., Dixon, M. M., Pattridge, K. A., Stallings, W. C., Fee, J. A., and Ludwig, M. L. (1995) *Biochemistry* 34:1646–1660.

Leatherbarrow, R. J. (1987) "Enzfitter: a nonlinear regression data analysis program for the IBM PC" Elsevier BIOSOFT, Cambridge.

Lepock, J. R., Ritchie, K. P., Kolios, M. C., Rodahl, A. M., Heinz, K. and Kruuv, J. (1992) *Biochemistry* 31:12706–12712.

Ludwig, M. L., Metzger, A. L., Pattridge, K. A., and Stallings, W. C. (1991) *J. Mol. Biol.* 219:335–358.

McAdam, M. E., Fox, R. A., Lavelle, F., Fielden, E. M. (1977a) *Biochem. J.* 165:71–79.

McAdam, M. E., Lavelle, F., Fox, R. A., Fielden, E. M. (1977b) *Biochem J.* 165:81–97.

McClune, G. J., and Fee, J. A. (1978) *Biophysical J.* 24:65–69.

McCord, J. M., Boyle, J. A., Bay, E. D., Rizzolo, L. J., and Salin, M. L. (1977) In: Superoxide and Superoxide Dismutase. Michelson, A. M., McCord, J. M., and Fridovich, I. (Eds.) Academic Press, London, pp 129–138.

McRee, D. E. (1992) *J. Mol. Graphics* 10:44–47.

Otwinowski, Z. (1993) *Proceedings of the CCP, Study Weekend* January 29–30, 56.

Parker, M. W. and Blake, C. C. F. (1988) *J. Mol Biol.* 199:649–661.

Privalov, P. L., and Khechinashvili, N. N. (1974) *J. Mol. Biol.* 86:665–684.

Rabani, J., Nielson, S. O. (1969) *J. Phys. Chem.* 73:3736–3744.

Schwarz, H. A. (1981) *J. Chem. Ed.* 58:101–105.

Shoichet, B. K., Baase, W. A., Kuroki, R., and Matthews, B. W. (1995) *Proc. Natl. Acad. Sci. USA* 92:452–456.

Smith, M. W. and Doolittle, R. F. (1992) *J. Molec. Evolution* 34:175–184.

Stephens, P. J., Jollie, D. R., and Warshel, A. (1996) *Chem. Rev.* 96:2491–2513.

Stoddard, B. L., Ringe, D., and Petsko, G. A. (1990) *Protein Engineering* 4:113–119.

Sturtevant, J. M. (1987) *Ann Rev. Phys. Chem.* 38:463–488.

Valentine, J. S. and Curtis, A. B. 1975) *J. Am. Chem. Soc.* 97:224–226.

Wagner, U. G., Pattridge, K. A., Ludwig, M. L., Stallings, W. C., Werber, M. M., Oefiner, C., Frolow, F., Sussman, J. L. (1993) *Protein Sci.* 2:814–825.

Whittaker, J. W., and Whittaker, M. M. (1991) *J. Am. Chem. Soc.* 113:5528–5540.

---

What is claimed is:

1. A nucleic acid encoding a human manganese superoxide dismutase protein having catalytic activity which differs from natural human manganese superoxide dismutase in that it exhibits reduced or no product inhibition compared to natural human manganese superoxide dismutase.

2. The nucleic acid of claim 1 comprising a nucleotide sequence which encodes a protein which differs in amino acid sequence from the sequence shown in SEQ ID NO:2, or the mature portion thereof, by the substitution, addition or deletion of one or more amino acids within or interactive with the active site of the protein.

3. The nucleic acid of claim 2 wherein said substitution of said one or more amino acids comprises replacement with an amino acid selected from the group consisting of a charged amino acid capable of proton donation and a smaller amino acid.

4. The nucleic acid of claim 2 comprising a nucleotide sequence which encodes a protein which differs in amino acid sequence from the sequence shown in SEQ ID NO:2, or the mature portion thereof, by substitution of an amino acid selected from the group consisting of His 26, His 30, His 74, Tyr 34, Gln 143, Asp 159, Trp 161 and His 163.

5. The nucleic acid of claim 4 encoding an amino acid sequence which differs from the sequence shown in SEQ ID NO:2, or the mature portion thereof, by substitution of Gln 143 with an amino acid sequence selected from the group consisting of Ala, Asn, His, Asp and Glu.

6. A nucleic acid encoding the amino acid sequence shown in SEQ ID NO:3, or the mature portion thereof.

7. The nucleic acid of claim 2 comprising a nucleotide sequence which encodes a protein which differs in amino acid sequence from the sequence shown in SEQ ID NO:2, or the mature portion thereof, in that Gln 143 has been replaced by an amino acid selected from the group consisting of an amino acid which is conservative with Gln, an amino acid which is smaller than Gln and an amino acid capable of protein donation.

8. An expression vector comprising the nucleic acid of claim 1 operably linked to a promoter.

9. An expression vector comprising the nucleic acid of claim 2 operably linked to a promoter.

10. The expression vector of claim 9 wherein the promoter is a mammalian promoter.

11. A method of protecting a cell from damage caused by peroxide radicals comprising transfecting the cell with an expression vector of claim 8.

12. A method of treating a subject suffering from cytotoxicity caused by superoxide radicals, comprising administering to the subject a composition comprising the expression vector of claim 8 and a pharmaceutically acceptable carrier.

13. The method of claim 12 wherein the subject is suffering from inflammation.

14. The method of claim 12 wherein the subject is suffering from reperfusion injury following ischemia.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 813 base pairs
      (B) TYPE: nucleic acid
      (C) STRANDEDNESS: single
      (D) TOPOLOGY: linear

```
    (ii) MOLECULE TYPE: cDNA (ix) FEATURE:
         (A) NAME/KEY: CDS
         (B) LOCATION: 43..708

(ix) FEATURE:
         (A) NAME/KEY: mat_peptide
         (B) LOCATION: 115..708

(xi) SEQUENCE DESCRIPTION: SEQ ID NO:1:

GAATTCGGCG GCGGCATCAG CGGCTAAGCC AGCACTAGCA GC ATG TTG AGC CGG            54
                                              Met Leu Ser Arg
                                                     -24

GCA GTG TGC GGC ACC AGC AGG CAG CTG GCT CCG GCT TTG GGG TAT CTG         102
Ala Val Cys Gly Thr Ser Arg Gln Leu Ala Pro Ala Leu Gly Tyr Leu
-20                 -15                 -10                  -5

GGC TCC AGG CAG AAG CAC AGC CTC CCC GAC CTG CCC TAC GAC TAC GGC         150
Gly Ser Arg Gln Lys His Ser Leu Pro Asp Leu Pro Tyr Asp Tyr Gly
                 1               5                  10

GCC CTG GAA CCT CAC ATC AAC GCG CAG ATC ATG CAG CTG CAC CAC AGC         198
Ala Leu Glu Pro His Ile Asn Ala Gln Ile Met Gln Leu His His Ser
            15                  20                  25

AAG CAC CAC GCG GCC TAC GTG AAC AAC CTG AAC GTC ACC GAG GAG AAG         246
Lys His His Ala Ala Tyr Val Asn Asn Leu Asn Val Thr Glu Glu Lys
        30                  35                  40

TAC CAG GAG GCG TTG GCC AAG GGA GAT GTT ACA GCC CAG ATA GCT CTT         294
Tyr Gln Glu Ala Leu Ala Lys Gly Asp Val Thr Ala Gln Ile Ala Leu
45                  50                  55                  60

CAG CCT GCA CTG AAG TTC AAT GGT GGT GGT CAT ATC AAT CAT AGC ATT         342
Gln Pro Ala Leu Lys Phe Asn Gly Gly Gly His Ile Asn His Ser Ile
                65                  70                  75

TTC TGG ACA AAC CTC AGC CCT AAC GGT GGT GGA GAA CCC AAA GGG GAG         390
Phe Trp Thr Asn Leu Ser Pro Asn Gly Gly Gly Glu Pro Lys Gly Glu
            80                  85                  90

TTG CTG GAA GCC ATC AAA CGT GAC TTT GGT TCC TTT GAC AAG TTT AAG         438
Leu Leu Glu Ala Ile Lys Arg Asp Phe Gly Ser Phe Asp Lys Phe Lys
        95                  100                 105

GAG AAG CTG ACG GCT GCA TCT GTT GGT GTC CAA GGC TCA GGT TGG GGT         486
Glu Lys Leu Thr Ala Ala Ser Val Gly Val Gln Gly Ser Gly Trp Gly
    110                 115                 120

TGG CTT GGT TTC AAT AAG CAA CGG GGA CAC TTA CAA ATT GCT GCT TGT         534
Trp Leu Gly Phe Asn Lys Gln Arg Gly His Leu Gln Ile Ala Ala Cys
125                 130                 135                 140

CCA AAT CAG GAT CCA CTG CAA GGA ACA ACA GGC CTT ATT CCA CTG CTG         582
Pro Asn Gln Asp Pro Leu Gln Gly Thr Thr Gly Leu Ile Pro Leu Leu
                145                 150                 155

GGG ATT GAT GTG TGG GAG CAC GCT TAC TAC CTT CAG TAT AAA AAT GTC         630
Gly Ile Asp Val Trp Glu His Ala Tyr Tyr Leu Gln Tyr Lys Asn Val
            160                 165                 170

AGG CCT GAT TAT CTA AAA GCT ATT TGG AAT GTA ATC AAC TGG GAG AAT         678
Arg Pro Asp Tyr Leu Lys Ala Ile Trp Asn Val Ile Asn Trp Glu Asn
        175                 180                 185

GTA ACT GAA AGA TAC ATG GCT TGC AAA AAG TAAACCACGA TCGTTATGCT           728
Val Thr Glu Arg Tyr Met Ala Cys Lys Lys
190                 195

GATCATACCC TAATGATCCC AGCAAGATAA TGTCCTGTCT TCTAAGATGT GCATCAAGCC       788

TGGGTACATA CTGAAACCCC GAATT                                             813

(2) INFORMATION FOR SEQ ID NO:2:

(i) SEQUENCE CHARACTERISTICS:
```

(A) LENGTH: 222 amino acids
            (B) TYPE: amino acid
            (D) TOPOLOGY: linear (ii) MOLECULE TYPE: protein (ix) FEATURE:
            (A) NAME/KEY: OTHER
            (B) LOCATION: 131
            (D) OTHER INFORMATION: Xaa can code for Gln or Glu (xi) SEQUENCE DESCRIPTION: SEQ ID NO:2:

Met Leu Ser Arg Ala Val Cys Gly Thr Ser Arg Gln Leu Ala Pro Ala
-24             -20                 -15                 -10

Leu Gly Tyr Leu Gly Ser Arg Gln Lys His Ser Leu Pro Asp Leu Pro
             -5                   1               5

Tyr Asp Tyr Gly Ala Leu Glu Pro His Ile Asn Ala Gln Ile Met Gln
         10              15                  20

Leu His His Ser Lys His His Ala Ala Tyr Val Asn Asn Leu Asn Val
     25              30              35                  40

Thr Glu Glu Lys Tyr Gln Glu Ala Leu Ala Lys Gly Asp Val Thr Ala
             45              50              55

Gln Ile Ala Leu Gln Pro Ala Leu Lys Phe Asn Gly Gly His Ile
             60              65              70

Asn His Ser Ile Phe Trp Thr Asn Leu Ser Pro Asn Gly Gly Gly Glu
         75              80              85

Pro Lys Gly Glu Leu Leu Glu Ala Ile Lys Arg Asp Phe Gly Ser Phe
     90              95                  100

Asp Lys Phe Lys Glu Lys Leu Thr Ala Ala Ser Val Gly Val Gln Gly
105             110             115                 120

Ser Gly Trp Gly Trp Leu Gly Phe Asn Lys Xaa Arg Ala His Leu Gln
             125             130             135

Ile Ala Ala Cys Pro Asn Gln Asp Pro Leu Gln Gly Thr Thr Gly Leu
             140             145             150

Ile Pro Leu Leu Gly Ile Asp Val Trp Glu His Ala Tyr Tyr Leu Gln
         155             160             165

Tyr Lys Asn Val Arg Pro Asp Tyr Leu Lys Ala Ile Trp Asn Val Ile
     170             175             180

Asn Trp Glu Asn Val Thr Glu Arg Tyr Met Ala Cys Lys Lys
185             190             195

(2) INFORMATION FOR SEQ ID NO:3:

(i) SEQUENCE CHARACTERISTICS:
            (A) LENGTH: 222 amino acids
            (B) TYPE: amino acid
            (D) TOPOLOGY: linear (ii) MOLECULE TYPE: protein (ix) FEATURE:
            (A) NAME/KEY: OTHER
            (B) LOCATION: 131
            (C) OTHER INFORMATION: Xaa can code for Gln or Glu (xi) SEQUENCE DESCRIPTION: SEQ ID NO:3:

Met Leu Ser Arg Ala Val Cys Gly Thr Ser Arg Gln Leu Ala Pro Ala
-24             -20                 -15                 -10

Leu Gly Tyr Leu Gly Ser Arg Gln Lys His Ser Leu Pro Asp Leu Pro
             -5                   1               5

Tyr Asp Tyr Gly Ala Leu Glu Pro His Ile Asn Ala Gln Ile Met Gln
         10              15                  20

Leu His His Ser Lys His His Ala Ala Tyr Val Asn Asn Leu Asn Val
 25                  30                  35                  40

Thr Glu Glu Lys Tyr Gln Glu Ala Leu Ala Lys Gly Asp Val Thr Ala
                 45                  50                  55

Gln Ile Ala Leu Gln Pro Ala Leu Lys Phe Asn Gly Gly His Ile
             60                  65                  70

Asn His Ser Ile Phe Trp Thr Asn Leu Ser Pro Asn Gly Gly Gly Glu
         75                  80                  85

Pro Lys Gly Glu Leu Leu Glu Ala Ile Lys Arg Asp Phe Gly Ser Phe
     90                  95                 100

Asp Lys Phe Lys Glu Lys Leu Thr Ala Ala Ser Val Gly Val Gln Gly
105                 110                 115                 120

Ser Gly Trp Gly Trp Leu Gly Phe Asn Lys Xaa Arg Ala His Leu Gln
                125                 130                 135

Ile Ala Ala Cys Pro Asn Asn Asp Pro Leu Gln Gly Thr Thr Gly Leu
            140                 145                 150

Ile Pro Leu Leu Gly Ile Asp Val Trp Glu His Ala Tyr Tyr Leu Gln
            155                 160                 165

Tyr Lys Asn Val Arg Pro Asp Tyr Leu Lys Ala Ile Trp Asn Val Ile
        170                 175                 180

Asn Trp Glu Asn Val Thr Glu Arg Tyr Met Ala Cys Lys Lys
185                 190                 195

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCATATGAAG CACAGCCTCC                                                   20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGAGATCTCA GCATAACGAT C                                                 21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCAGCTTACT GTATTCTGCA G                                                 21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CCTTTAAACA CAGCCTCCCC G                                                21

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCTTGTCCAA ATAACGATCC ACTGC                                     25

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

AGTGGATCGT TATTTGGACA AGC                                       23

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CCACGCGGCC TTCGTTAACA ACCTG                                     25

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CAGGTTGTTA ACGAAGGCCG CGTGG                                     25